US012565491B2

(12) United States Patent
Kim et al.

(10) Patent No.: US 12,565,491 B2
(45) Date of Patent: Mar. 3, 2026

(54) (ISOPROPYL-TRIAZOLYL)PYRIDINYL-SUBSTITUTED BENZOOXAZINONE OR BENZOTHIAZINONE DERIVATIVES AND USE THEREOF

(71) Applicant: HK INNO.N CORPORATION, Seoul (KR)

(72) Inventors: Dongkyu Kim, Suwon-si (KR); Seungin Kim, Suwon-si (KR); Jaeho Yoo, Hwaseong-si (KR); Seunghee Ji, Suwon-si (KR); Joo-hwan Kim, Seongnam-si (KR); Joonseok Byun, Suwon-si (KR); Jinwoo Jung, Seoul (KR); Soo-jin Kim, Suwon-si (KR); Yeji Byeon, Suwon-si (KR); Jiwon Choi, Icheon-si (KR)

(73) Assignee: HK INNO.N CORPORATION, Seoul (KR)

( * ) Notice: Subject to any disclaimer, the term of this patent is extended or adjusted under 35 U.S.C. 154(b) by 910 days.

(21) Appl. No.: 17/277,313

(22) PCT Filed: Oct. 10, 2019

(86) PCT No.: PCT/KR2019/013312

§ 371 (c)(1),
(2) Date: Mar. 18, 2021

(87) PCT Pub. No.: WO2020/080742

PCT Pub. Date: Apr. 23, 2020

(65) Prior Publication Data

US 2022/0033390 A1 Feb. 3, 2022

(30) Foreign Application Priority Data

Oct. 18, 2018 (KR) ........................ 10-2018-0124731

(51) Int. Cl.

| | |
|---|---|
| ***C07D 413/14*** | (2006.01) |
| ***C07D 417/14*** | (2006.01) |
| *C07D 265/14* | (2006.01) |
| *C07D 279/08* | (2006.01) |

(52) U.S. Cl.

CPC ......... *C07D 413/14* (2013.01); *C07D 417/14* (2013.01)

(58) Field of Classification Search

CPC .. C07D 413/14; C07D 417/14; C07D 279/08; C07D 277/62; C07D 279/16

USPC ........................................................ 514/244.2

See application file for complete search history.

(56) References Cited

U.S. PATENT DOCUMENTS 5,189,034 A * 2/1993 Alberto et al. ........ A61K 31/54 514/224.2

FOREIGN PATENT DOCUMENTS

| | | | | |
|---|---|---|---|---|
| JP | H05-32642 A | 2/1993 | | |
| WO | WO2012154760 A1 * | 11/2012 | | C07D 237/32 |
| WO | WO2016208775 A1 * | 12/2016 | | C07D 413/14 |
| WO | 2018/133865 A1 | 7/2018 | | |
| WO | 2018/149284 A1 | 8/2018 | | |
| WO | 2018/151830 A1 | 8/2018 | | |
| WO | 2018/157857 A1 | 9/2018 | | |
| WO | WO2018157227 A1 * | 9/2018 | | C07D 453/06 |
| WO | WO 2018157277 A1 * | 9/2018 | | C07D 453/06 |
| WO | WO2018183122 A1 * | 10/2018 | | C07D 401/04 |
| WO | WO2019015559 A1 * | 1/2019 | | C07D 401/14 |

OTHER PUBLICATIONS

CAS Reaction_20240717_1619, SciFinder, Retrieved Jul. 2024. (Year: 2024).*

Translation of Wang (WO2019015559A1), google patents, retrieved Jul. 2024. (Year: 2024).*

International Search Report issued in corresponding International Patent Application No. PCT/KR2019/013312 dated Jan. 20, 2020.

Written Opinion issued in corresponding International Patent Application No. PCT/KR2019/013312 dated Jan. 20, 2020.

Office Action issued Apr. 25, 2024 for Chinese Patent Application No. 201980067466.4.

* cited by examiner

*Primary Examiner* — Jeffrey S Lundgren
*Assistant Examiner* — Heather Dahlin
(74) *Attorney, Agent, or Firm* — Morgan, Lewis & Bockius LLP

(57) ABSTRACT

The present disclosure relates to novel (isopropyl-triazolyl) pyridinyl-substituted benzooxazinone or benzothiazinone derivatives, or a pharmaceutically acceptable salt thereof; a preparation method thereof; and use for preventing or treating an ASK-1 mediated disease comprising the same as an active ingredient.

20 Claims, No Drawings

(ISOPROPYL-TRIAZOLYL)PYRIDINYL-SUBSTITUTED BENZOOXAZINONE OR BENZOTHIAZINONE DERIVATIVES AND USE THEREOF

TECHNICAL FIELD

The present disclosure relates to novel (isopropyl-triazolyl)pyridinyl-substituted benzooxazinone or benzothiazinone derivatives, or a pharmaceutically acceptable salt thereof; a preparation method thereof; and use for preventing or treating an ASK-1 mediated disease by dysregulation of the comprising the same as an active ingredient.

BACKGROUND ART

Mitogen-activated protein kinase (MAPK) signaling cascades involve in directing various extracellular and intracellular queues to cellular stress responses, including cell growth, differentiation, inflammation, and apoptosis. MAPKs exist in different types such as MAP3Ks, MAP2Ks, and MAPKs. MAPK3s directly respond to environmental signals and phosphorylate MAP2Ks, which in turn phosphorylates specific MAPKs. Subsequently, MAPKs serve to mediate appropriate cellular responses by phosphorylating cellular substrates, including transcription factors that regulate gene expression.

Apoptosis signal-regulating kinase 1 (ASK1), which is also known as a mitogen-activated protein kinase kinase kinase 5 (MAP3K5), is a member of the MAP kinase kinase kinase (MAP3K) family that activates the c-Jun N-terminal protein kinase (JNK) and p38 MAP kinase.

ASK1 is activated by a series of various stimuli including oxidative stress, reactive oxygen species (ROS), LPS, TNF-α, FasL, endoplasmic reticulum (ER) stress, and intracellular calcium influx, and consequently activates the c-Jun N-terminal protein kinase (JNK) and p38 MAP kinase.

Phosphorylation of ASK1 protein can lead to apoptosis or other cellular responses depending on the cell type. ASK1 activation has been reported to be associated with a broad range of diseases including neurodegenerative diseases, cardiovascular diseases, inflammatory diseases, autoimmune diseases, and metabolic disorders. In addition, ASK1 has been implicated to particularly play a vital role in psychosomatic diseases, for example, kidney diseases, diabetic nephropathy, chronic kidney diseases, fibrosis (including lung fibrosis and kidney fibrosis), respiratory diseases (including chronic obstructive pulmonary disease (COPD) and acute lung injury), and acute and chronic liver diseases.

Therefore, development of therapeutic agents that function to inhibit ASK1 signaling complexes is expected to remedy or improve the lives of patients in need of prevention and treatment of such a broad range of diseases.

DISCLOSURE OF INVENTION

Technical Problem

The present inventors have made extensive efforts to develop novel compounds that can inhibit ASK-1 activity, and as a result, they have confirmed that a series of (isopropyl-triazolyl)pyridinyl-substituted benzooxazinone or benzothiazinone derivative can effectively inhibit ASK-1 activity and thus can be useful in the prevention and treatment of an ASK-1 mediated disease, thereby completing the present invention.

Solution to Problem

An object of the present disclosure is to provide (isopropyl-triazolyl)pyridinyl-substituted benzooxazinone or benzothiazinone derivatives or pharmaceutically acceptable salts thereof.

Another object of the present disclosure is to provide a method for preparing the aforementioned (isopropyl-triazolyl)pyridinyl-substituted benzooxazinone or benzothiazinone derivatives.

Still another object of the present disclosure is to provide a pharmaceutical composition for preventing or treating an ASK-1 mediated disease, including the aforementioned (isopropyl-triazolyl)pyridinyl-substituted benzooxazinone or benzothiazinone derivatives or pharmaceutically acceptable salts thereof as an active ingredient.

Still another object of the present disclosure is to provide a method for preventing or treating an ASK-1 mediated disease, including administering the aforementioned pharmaceutical composition to a subject in need thereof.

Advantageous Effects of Invention

The novel (isopropyl-triazolyl)pyridinyl-substituted benzooxazinone or benzothiazinone derivatives or pharmaceutically acceptable salts thereof exhibit an inhibitory effect against ASK-1 activity and thus can be effectively used in the prevention and treatment of an ASK-1 mediated disease.

BEST MODE FOR CARRYING OUT THE INVENTION

In one aspect of the present disclosure to achieve the above objects, there is provides (isopropyl-triazolyl)pyridinyl-substituted benzooxazinone or benzothiazinone derivatives or pharmaceutically acceptable salts thereof.

In another aspect of the present disclosure, there is provided a method for preparing the (isopropyl-triazolyl) pyridinyl-substituted benzooxazinone or benzothiazinone derivatives.

In still another aspect of the present disclosure, there is provided a pharmaceutical composition for preventing or treating an ASK-1 mediated disease, including the (isopropyl-triazolyl)pyridinyl-substituted benzooxazinone or benzothiazinone derivatives or pharmaceutically acceptable salts thereof as an active ingredient.

In still further another aspect of the present disclosure, there is provided a method for preventing or treating an ASK-1 mediated disease, including administering the pharmaceutical composition to a subject in need thereof.

Hereinbelow, the present disclosure will be described in detail.

Listed below are definitions of various concepts used to describe the compounds of the present disclosure.

These definitions apply to the terms used throughout this specification, unless otherwise limited in specific instances, either individually or as part of a larger group.

The term "alkyl" refers to a straight, branched or cyclic hydrocarbon radical, and each carbon atom may be optionally substituted with one or more substituents.

The term "alkoxy" refers to —O-alkyl, and the alkyl is as defined above.

The term "aryl" refers to an aromatic group including phenyl, naphthyl and the like. Aryl may be optionally substituted with one or more substituents.

The term "heteroaryl" refers to a saturated, partially saturated or aromatic group containing 1 to 4 heteroatoms selected from N, O and S, which can be optionally fused with benzo or cycloalkyl.

The term "halo(gen)" refers to a substituent selected from the group consisting of fluoro, chloro, bromo or iodo.

The terms and abbreviations used herein have their original meanings unless defined otherwise.

The (isopropyl-triazolyl)pyridinyl-substituted benzoxazinone or benzothiazinone derivative of the present disclosure may be a compound represented by Chemical Formula 1 below:

[Chemical Formula 1]

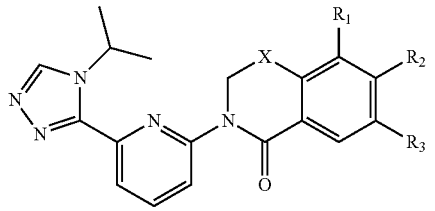

in the Chemical Formula 1 above,

X is O or S;

$R_1$ is hydrogen, $C_{1-6}$ alkyl, $C_{1-6}$ heteroalkyl, $C_{1-6}$ alkoxy, or halogen;

$R_2$ and $R_3$ are each independently hydrogen, $C_{1-6}$ alkyl, $C_{1-6}$ heteroalkyl, $C_{1-6}$ alkoxy, halogen, cyano, nitro, amino, $C_{6-10}$ aryl, $C_{6-10}$ arylamino, $C_{5-10}$ heteroaryl, or $C_{5-10}$ heteroarylamino; and the aryl or heteroaryl is unsubstituted, or is substituted with at least one selected from the group consisting of $C_{1-6}$ alkyl, $C_{1-6}$ alkoxy, $C_{1-6}$ alkoxy-$C_{1-6}$ alkyl, halogen, nitro, cyano, amino, $C_{1-6}$ alkylamino, acetylamino, formyl, $C_{1-6}$ alkylcarbonyl, morpholinocarbonyl, morpholinyl, piperazinyl, piperidinyl, aminocarbonyl, $C_{1-6}$ alkylaminocarbonyl, di($C_{1-6}$ alkyl) aminocarbonyl, $C_{1-6}$ alkylthio, cyano-$C_{1-6}$ alkyl, $C_{1-6}$ haloalkyl, $C_{1-6}$ dihaloalkyl, $C_{1-6}$ alkylsulfonyl, aminosulfonyl, $C_{1-6}$ alkylaminosulfonyl, di($C_{1-6}$ alkyl) aminosulfonyl, $C_{1-6}$heteroalkyl, and heteroaryl-$C_{1-6}$ alkyl.

For example, in the Chemical Formula 1 above, $R_1$ may be hydrogen, and $R_2$ may be hydrogen or $C_{1-6}$ alkyl.

Specifically, in the Chemical Formula 1 above, $R_1$ may be hydrogen, and $R_2$ may be hydrogen or methyl.

Specifically, in the Chemical Formula 1 above, $R_3$ may be substituted or unsubstituted phenyl, imidazolyl, pyrazolyl, pyridinyl, pyrimidinyl, or pyrimidinylamino.

For example, in the compound of the present disclosure, the aryl or heteroaryl may be unsubstituted, or may be substituted with at least one selected from the group consisting of methyl, isopropyl, isobutyl, isopentyl, cyclopropyl, cyclopropylmethyl, ethoxyethyl, difluoromethyl, cyanocyclopropyl, methylthio, methylsulfonyl, tetrahydrofuranyl, and pyrazolylmethyl. However, the present disclosure is not limited thereto.

More specifically, the compound of the present disclosure may be 1. 6-(1-(cyclopropylmethyl)-1H-pyrazol-4-yl)-3-(6-(4-isopropyl-4H-1,2,4-triazol-3-yl)pyridin-2-yl)-2,3-dihydro-4H-benzo[e][1,3]oxazin-4-one,
2. 3-(6-(4-isopropyl-4H-1,2,4-triazol-3-yl)pyridin-2-yl)-6-(4-(methylsulfonyl)phenyl)-2,3-dihydro-4H-benzo[e][1,3]oxazin-4-one,
3. 3-(6-(4-isopropyl-4H-1,2,4-triazol-3-yl)pyridin-2-yl)-6-(pyridin-4-yl)-2,3-dihydro-4H-benzo[e][1,3]oxazin-4-one,
4. 3-(6-(4-isopropyl-4H-1,2,4-triazol-3-yl)pyridin-2-yl)-6-(4-methylpyrimidin-2-ylamino)-2,3-dihydro-4H-benzo[e][1,3]oxazin-4-one,
5. 3-(6-(4-isopropyl-4H-1,2,4-triazol-3-yl)pyridin-2-yl)-6-(1-(tetrahydrofuran-3-yl)-1H-pyrazol-4-yl)-2,3-dihydro-4H-benzo[e][1,3]oxazin-4-one,
6. 6-(1-(1-ethoxyethyl)-1H-pyrazol-4-yl)-3-(6-(4-isopropyl-4H-1,2,4-triazol-3-yl)pyridin-2-yl)-2,3-dihydro-4H-benzo[e][1,3]oxazin-4-one,
7. 6-(1-(difluoromethyl)-1H-pyrazol-4-yl)-3-(6-(4-isopropyl-4H-1,2,4-triazol-3-yl)pyridin-2-yl)-2,3-dihydro-4H-benzo[e][1,3]oxazin-4-one,
8. 6-(1-cyclopropyl-1H-pyrazol-4-yl)-3-(6-(4-isopropyl-4H-1,2,4-triazol-3-yl)pyridin-2-yl)-2,3-dihydro-4H-benzo[e][1,3]oxazin-4-one,
9. 6-(1-isobutyl-1H-pyrazol-4-yl)-3-(6-(4-isopropyl-4H-1,2,4-triazol-3-yl)pyridin-2-yl)-2,3-dihydro-4H-benzo[e][1,3]oxazin-4-one,
10. 6-(4-(difluoromethyl)pyrimidin-2-ylamino)-3-(6-(4-isopropyl-4H-1,2,4-triazol-3-yl)pyridin-2-yl)-2,3-dihydro-4H-benzo[e][1,3]oxazin-4-one,
11. 6-(1-isopentyl-1H-pyrazol-4-yl)-3-(6-(4-isopropyl-4H-1,2,4-triazol-3-yl)pyridin-2-yl)-2,3-dihydro-4H-benzo[e][1,3]oxazin-4-one,
12. 1-(4-(3-(6-(4-isopropyl-4H-1,2,4-triazol-3-yl)pyridin-2-yl)-4-oxo-3,4-dihydro-2H-benzo[e][1,3]oxazin-6-yl)phenyl)cyclopropanecarbonitrile,
13. 6-(4-((1H-pyrazol-1-yl)methyl)phenyl)-3-(6-(4-isopropyl-4H-1,2,4-triazol-3-yl)pyridin-2-yl)-2,3-dihydro-4H-benzo[e][1,3]oxazin-4-one,
14. 6-(1-(cyclopropylmethyl)-1H-pyrazol-4-yl)-3-(6-(4-isopropyl-4H-1,2,4-triazol-3-yl)pyridin-2-yl)-7-methyl-2,3-dihydro-4H-benzo[e][1,3]oxazin-4-one,
15. 6-(1-isopropyl-1H-pyrazol-4-yl)-3-(6-(4-isopropyl-4H-1,2,4-triazol-3-yl)pyridin-2-yl)-7-methyl-2,3-dihydro-4H-benzo[e][1,3]oxazin-4-one,
16. 3-(6-(4-isopropyl-4H-1,2,4-triazol-3-yl)pyridin-2-yl)-7-methyl-6-(pyrimidin-5-yl)-2,3-dihydro-4H-benzo[e][1,3]oxazin-4-one,
17. 3-(6-(4-isopropyl-4H-1,2,4-triazol-3-yl)pyridin-2-yl)-7-methyl-6-(2-(methylthio)pyrimidin-5-yl)-2,3-dihydro-4H-benzo[e][1,3]oxazin-4-one,
18. 3-(6-(4-isopropyl-4H-1,2,4-triazol-3-yl)pyridin-2-yl)-7-methyl-6-(1-(tetrahydrofuran-3-yl)-1H-pyrazol-4-yl)-2,3-dihydro-4H-benzo[e][1,3]oxazin-4-one,
19. 6-(4-cyclopropyl-1H-imidazol-1-yl)-3-(6-(4-isopropyl-4H-1,2,4-triazol-3-yl)pyridin-2-yl)-2,3-dihydro-4H-benzo[e][1,3]oxazin-4-one,
20. 6-(1-(1-ethoxyethyl)-1H-pyrazol-4-yl)-3-(6-(4-isopropyl-4H-1,2,4-triazol-3-yl)pyridin-2-yl)-7-methyl-2,3-dihydro-4H-benzo[e][1,3]oxazin-4-one,
21. 6-(1-(cyclopropylmethyl)-1H-pyrazol-4-yl)-3-(6-(4-isopropyl-4H-1,2,4-triazol-3-yl)pyridin-2-yl)-2,3-dihydro-4H-benzo[e][1,3]thiazin-4-one,
22. 6-(1-isopropyl-1H-pyrazol-4-yl)-3-(6-(4-isopropyl-4H-1,2,4-triazol-3-yl)pyridin-2-yl)-2,3-dihydro-4H-benzo[e][1,3]thiazin-4-one,
23. 6-(2-cyclopropylpyrimidin-5-yl)-3-(6-(4-isopropyl-4H-1,2,4-triazol-3-yl)pyridin-2-yl)-2,3-dihydro-4H-benzo[e][1,3]thiazin-4-one,
24. 6-(1-cyclopropyl-1H-pyrazol-4-yl)-3-(6-(4-isopropyl-4H-1,2,4-triazol-3-yl)pyridin-2-yl)-2,3-dihydro-4H-benzo[e][1,3]thiazin-4-one, or 25. 3-(6-(4-isopropyl-4H-1,2,4-triazol-3-yl)pyridin-2-yl)-6-(2-methylpyrimidin-5-yl)-2,3-dihydro-4H-benzo[e][1,3]thiazin-4-one, but is not limited to.

In addition, the compound of the present disclosure may exist in the form of a pharmaceutically acceptable salt. An acid-addition salt formed by a pharmaceutically acceptable free acid may be useful as the salt. As used herein, the term "pharmaceutically acceptable salt" refers to any organic or inorganic addition salt of the compound, which has a concentration such that it exhibits an effective action that is relatively nontoxic and harmless to patients and whose side effects caused by the salt do not impair the beneficial effect of the compound represented by Chemical Formula 1. The pharmaceutically acceptable salt may include an acid-addition salt formed by an acid that can form nontoxic acid-addition salt containing pharmaceutically acceptable anions, for example, inorganic acids such as hydrochloric acid, sulfuric acid, nitric acid, phosphoric acid, hydrobromic acid, hydroiodic acid and the like, organic carbonic acids such as tartaric acid, formic acid, citric acid, acetic acid, adipic acid, trichloroacetic acid, trifluoroacetic acid, gluconic acid, benzoic acid, lactic acid, fumaric acid, maleic acid and the like, or sulfonic acids such as methanesulfonic acid, benzenesulfonic acid, p-Toluenesulfonic acid or naphthalenesulfonic acid, and the like. The compound of Chemical Formula 1 according to the present disclosure can be converted into its salt by a conventional method.

The acid-addition salt may be prepared by a conventional method, for example, by dissolving a compound in an excessive amount of acid aqueous solution, followed by precipitating the salt using a water-miscible organic solvent such as methanol, ethanol, acetone or acetonitrile. An acid or alcohol (e.g., glycol monomethyl ether) in an equal molar amount of the compound and water may be heated, and subsequently, the mixture may be dried by evaporation, or the precipitated salt may be suction-filtered.

Further, a pharmaceutically acceptable metal salt may be prepared using a base. An alkali metal salt or an alkaline earth metal salt is obtained, for example, by dissolving a compound in an excessive amount of an alkali metal hydroxide or an alkaline earth metal hydroxide solution, followed by filtering undissolved compound salts, and evaporating and drying the filtrate.

The pharmaceutically acceptable salt of the compound of the present disclosure may include a salt of an acidic or a basic group, which can be present in the compound of Chemical Formula 1, unless otherwise specifically indicated, and may be prepared by a method of preparing salts known in the art.

In addition, the present disclosure is intended to include not only the compound of Chemical Formula 1 and a pharmaceutically acceptable salt thereof, but also possible solvates that may be prepared therefrom.

Further, since the compound of the present disclosure has an asymmetric carbon center in the parent structure and its substituent groups, it can exist as R- or S-isomers, racemic mixtures, diastereomers mixtures and individual diastereomers, and all of these isomers and mixtures thereof are within the scope of the present disclosure. That is, if the asymmetric carbon(s) is present in the structure of Chemical Formula 1, it is understood that all stereoisomers are included within the scope of the present disclosure, as long as the direction is not described separately.

The compound represented by Chemical Formula 1 of the present disclosure may be prepared according to a method including a step of reacting a compound represented by Chemical Formula 2 below with $R_3$-boronic acid or an $R_3$-halogen compound:

[Chemical Formula 2]

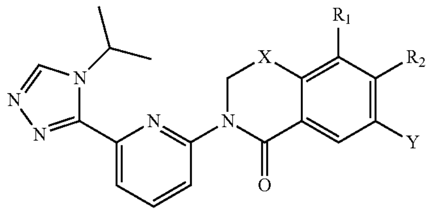

in the Chemical Formula 2 above,

X is O or S;

Y is halogen or amine; and $R_1$ to $R_3$ are as defined above.

Specifically, the reaction may be accomplished by a coupling reaction with a palladium(0) catalyst, but the present disclosure is not limited thereto.

The palladium(0) catalyst may be tetrakis(triphenylphosphine) palladium(0), and the reaction may be performed using a mixed solvent of dioxane and water as a solvent in the presence of potassium carbonate, but is not limited thereto. In this case, reaction temperature may be adjusted to 80° C. to 100° C., but is not limited thereto.

More specifically, the compound of Chemical Formula 1 of the present disclosure may be prepared according to Reaction Scheme 1 below.

[Reaction Scheme 1]

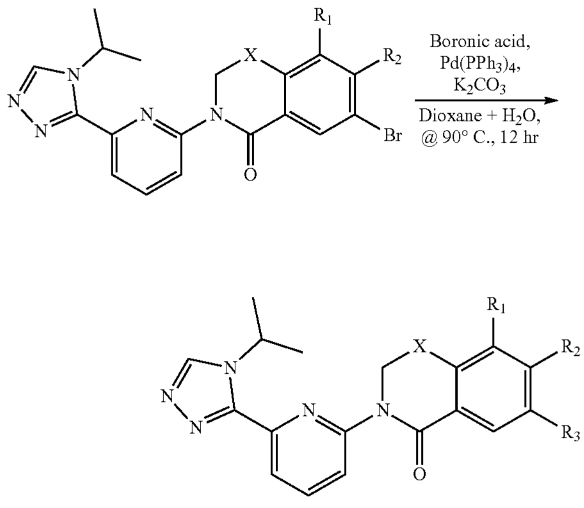

For example, when X is O in the Chemical Formula 2, the compound of Chemical Formula 2 may be prepared through a step a-1) of reacting 6-(4-isopropyl-4H-1,2,4-triazol-3-yl)pyridin-2-amine with 2-(benzyloxy)-3-$R_1$-4-$R_2$-5-Y-benzoic acid to obtain a compound of Chemical Formula 3 below, and a step a-2) of reacting the obtained compound with para-formaldehyde to cyclize to obtain an oxazine derivative compound represented by Chemical Formula 2:

[Chemical Formula 3]

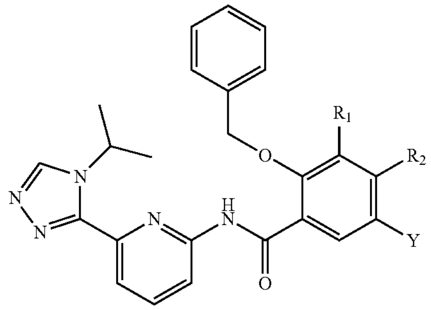

in the Chemical Formula 3 above

Y is halogen or nitro; and $R_1$ and $R_2$ are as defined above.

Specifically, the step a-1) may be performed in the presence of 1-[bis(dimethylamino)methylene]-1H-1,2,3-triazolo [4,5-b]pyridinium 3-oxide hexafluorophosphate (HATU) and a base, and the step a-2) may be performed by a cyclization reaction with para-formaldehyde. However, the present disclosure is not limited thereto.

More specifically, when Y is nitro, the reaction may further include a step a-3) of converting a nitro group into an amine group by a reduction reaction after the step a-2.

The base used in the step a-2) may be N-methylmorpholine, but is not limited thereto. Moreover, the step a-1) may be performed using N,N-dimethylformamide as a solvent, and the step a-2) may be performed using trifluoroacetic acid as a solvent, but the present disclosure is not limited thereto. In addition, reaction temperature may be adjusted to 80° C. to 100° C. in the step a-1), and may be adjusted to 90° C. to 110° C. in the step a-2), but the present disclosure is not limited thereto.

More specifically, in the method of preparing the compound of Chemical Formula 1 of the present disclosure, when X is O, the compound of Chemical Formula 2 may be prepared according to Reaction Scheme 2 below.

[Reaction Scheme 2]

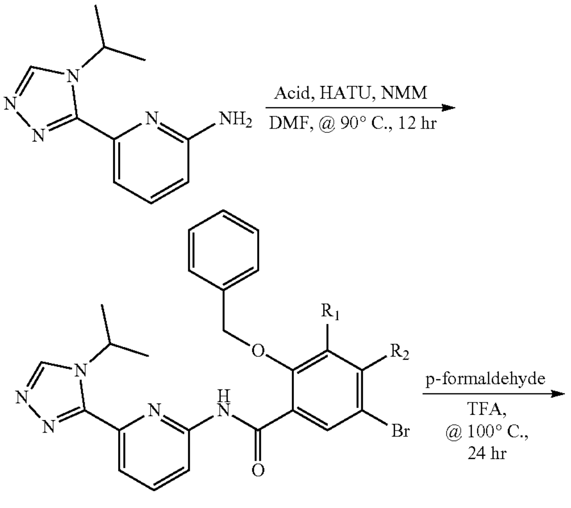

-continued

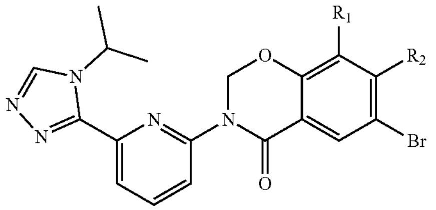

For example, when X is S in the Chemical Formula 2 above, the compound of Chemical Formula 2 above may be prepared through a step b-1) of reacting methyl 6-halopicolinate with hydrazine to obtain 6-halopicolinohydrazide, a step b-2) of reacting the 6-halopicolinohydrazide with dimethylformamide dimethyl acetal to obtain N'-(6-halopicolinoyl)-N,N-dimethylformohydrazonamide, a step b-3) of reacting the N'-(6-halopicolinoyl)-N,N-dimethylformohydrazonamide with isopropylamine to obtain 2-halo-6-(4-isopropyl-4H-1,2,4-triazol-3-yl)pyridine, and a step b-4) of reacting the 2-halo-6-(4-isopropyl-4H-1,2,4-triazol-3-yl) pyridine with 6-halo-2,3-dihydro-1,3-benzothiazin-4-one to obtain a thiazine derivative compound represented by Chemical Formula 2.

Specifically, the step b-1) may be performed in an ethanol solvent using hydrazine monohydrate at 70° C. to 110° C., the step b-2) may be performed in a N,N-dimethylformamide solvent at 80° C. to 120° C., the step b-3) may be performed in a mixed solvent of acetic acid and acetonitrile at 60° C. to 80° C., and the step b-4) may be performed in a N,N-dimethylformamide solvent in the presence of a palladium(0) catalyst, cesium carbonate, and 4,5-bis(diphenylphosphino)-9,9-dimethylxanthine at 80° C. to 100° C.

More specifically, in the method of preparing the compound of Chemical Formula 1 of the present disclosure, when X is S, the compound of Chemical Formula 2 may be prepared according to Reaction Scheme 3 below.

[Reaction Scheme 3]

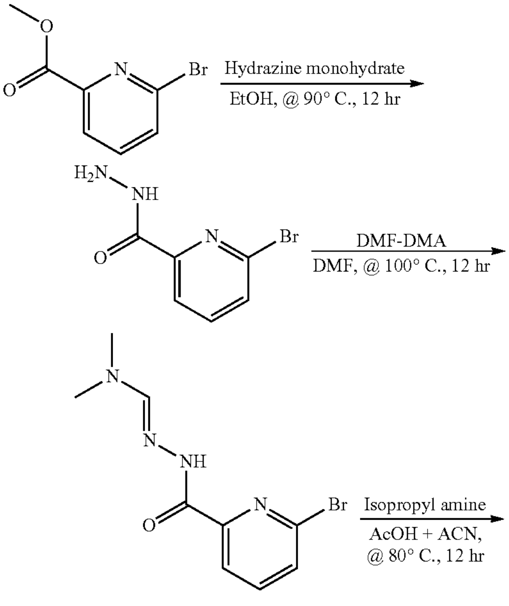

-continued

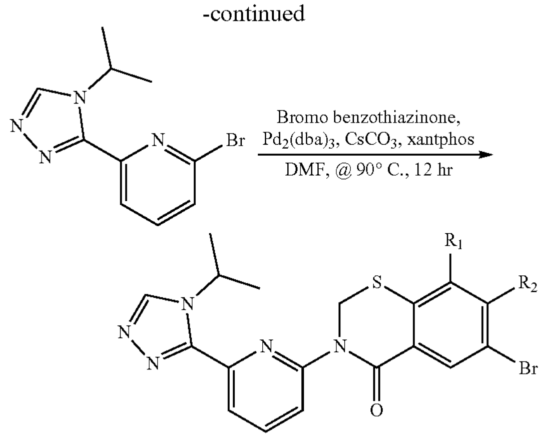

For example, after completion of each reaction, a separation and/or purification process may be further carried out in order to improve the efficiency of the reaction, or to increase the purity of the product. The separation and purification process can be carried out using any method known in the art without limitation.

Meanwhile, the above-described series of Reaction Schemes are merely provided for illustration of the preparation method of the compound of the present disclosure, and the preparation method of the compound of the present disclosure is not limited thereto, and may be carried out using methods known in the art or with appropriate modifications.

In addition, the present disclosure provides a pharmaceutical composition for preventing or treating an ASK-1 mediated disease, including the compound represented by Chemical Formula 1 or a pharmaceutically acceptable salt thereof as an active ingredient.

Further, the present disclosure provides a method for preventing or treating an ASK-1 mediated disease, including administering the pharmaceutical composition to a subject in need thereof.

Specifically, the compound of the present disclosure or a pharmaceutically acceptable salt thereof has a feature of inhibiting ASK-1 activity.

As used herein, the term "preventing" or "prevention" refers to all actions that suppress or delay the onset, spread and recurrence of the ASK-1 mediated diseases by the administration of the pharmaceutical composition. In addition, the term "treating" or "treatment" refers to all actions that alleviate or beneficially change the symptoms of the above disease by the administration of the pharmaceutical composition.

For example, the pharmaceutical composition according to the present disclosure may contain the compound represented by Chemical Formula 1 or a pharmaceutically acceptable salt thereof as an active ingredient in an amount of 0.1% to 75% by weight, specifically 1% to 50% by weight, based on the total weight of the composition.

The ASK-1 mediated diseases, which can be prevented or treated by administration of the pharmaceutical composition including the compound of Chemical Formula 1 according to the present disclosure may include diabetes, diabetic nephropathy, kidney disease, kidney fibrosis, lung fibrosis, idiopathic pulmonary fibrosis (IPF), liver fibrosis, pulmonary hypertension, chronic obstructive pulmonary disease (COPD), acute lung injury, nonalcoholic steatohepatitis, liver disease, alcoholic liver disease, alcoholic hepatitis, inflammatory condition, autoimmune disease, proliferative disease, transplantation rejection, a disease accompanying impairment of cartilage turnover, congenital cartilage malformation, or a disease associated with hypersecretion of IL6, but the disease is not limited thereto.

In a specific embodiment of the present disclosure, it was confirmed that the ASK-1 activity could be effectively inhibited by the administration of the compound of Chemical Formula 1 according to the present disclosure. Based on this finding, it was found that the compound of Chemical Formula 1 according to the present disclosure can be used for the prevention or treatment of diseases caused by ASK-1 activation.

As used herein, the term "subject" refers to all animals including monkeys, cattle, horses, sheep, pigs, chickens, turkeys, quails, cats, dogs, mice, rats, rabbits, or guinea pigs, as well as humans having the ASK-1 mediated disease or being at risk of having the same, and the disease may be effectively prevented or treated by administering the pharmaceutical composition of the present disclosure to the subject. The pharmaceutical composition of the present disclosure may be administered in combination with a conventional therapeutic agent.

As used herein, the term "administration" refers to the introduction of a predetermined substance to a patient by any appropriate method. The composition of the present disclosure may be administered via any common route as long as it can reach a desired tissue. The composition may be administered via an intraperitoneal route, an intravenous route, an intramuscular route, a subcutaneous route, an intradermal route, an oral route, a topical route, an intranasal route, an intrapulmonary route or an intrarectal route, but is not limited thereto. In addition, the pharmaceutical composition may be administered by any device capable of delivering the active component to the target cell.

The pharmaceutical composition according to the present disclosure may contain the compound represented by Chemical Formula 1 or a pharmaceutically acceptable salt thereof as an active ingredient, and may further include a pharmaceutically acceptable carrier, diluent, or excipient. As used herein, the term "pharmaceutically acceptable carrier or diluent" refers to a carrier or diluent which neither causes significant stimulation to an organism nor abolishes the biological activities or properties of a compound to be administered thereto. In addition, as used herein, the term "pharmaceutically acceptable excipient" refers to an inert material which is added to the pharmaceutical composition to facilitate the administration of the compound represented by Chemical Formula 1 of the present disclosure. Examples of the excipient may include calcium carbonate, calcium phosphate, various types of sugars and starches, cellulose derivatives, gelatin, vegetable oil, and polyethylene glycol, but are not limited thereto. Further, the composition may be prepared into various formulations including oral formulation such as powders, granules, tablets, capsules, suspensions, emulsions, syrups, aerosols, and the like, and injection of sterile injectable solution, and the like, according to conventional methods depending on the desired purpose.

The pharmaceutical composition of the present disclosure may be administered in a pharmaceutically effective amount or a therapeutically effective amount. As used herein, the term "pharmaceutically effective amount" refers to an amount sufficient to treat a disease at a reasonable benefit/risk ratio applicable to any medical treatment without causing an adverse effect, and the effective dosage level may be determined based on the factors including the heath condition of a patient, the type and severity of a disease, the activity of a drug, the sensitivity to a drug, an administration method, an administration time, an administration route and an excretion rate, a duration of treatment, drugs used simultaneously or in combination, and other factors well known in the medical field. In view of all the above elements, it is important to administer the composition at a dose at which the maximum effect can be achieved with the minimum amount without adverse effects. Thus, the dose of the composition may be easily determined by those skilled in the art. The daily dosage of the compound represented by Chemical Formula 1 or a pharmaceutically acceptable salt thereof may be specifically 1 mg/kg to 1000 mg/kg, and the composition may be administered once daily or several times a day as needed.

MODE FOR THE INVENTION

Hereinafter, preferred Examples are provided to help understanding of the present disclosure. However, these Examples are given for illustrative purposes only to help better understanding of the present disclosure, and the scope of the present disclosure is not intended to be limited to or by these Examples.

Various synthesis methods of starting materials for synthesizing the compound of the present disclosure have been known, and the starting materials may be purchased from the suppliers, if available on the market. Examples of the reagent suppliers include Sigma-Aldrich, TCI, Wako, Kanto, Fluorchem, Acros, Alfa, Fluka, Dae-Jung, Combi-Blocks, etc., but are not limited thereto. Further, all the commercially available materials were used without further purification unless specified otherwise.

First, the compounds used for syntheses in Examples were prepared according to Preparation Examples below. Preparation Examples are exemplary embodiments of the compound represented by Chemical Formula 1 in Reaction Scheme 1 above, and may be appropriately adjusted corresponding to the structures of the compounds in the Examples to be prepared.

Preparation Example 1: Preparation of 6-bromo-3-(6-(4-isopropyl-4H-1,2,4-triazol-3-yl)pyridin-2-yl)-2,3-dihydro-4H-benzo[e][1,3]oxazin-4-one

Step 1-1) Preparation of 2-(benzyloxy)-5-bromo-N-(6-(4-isopropyl-4H-1,2,4-triazol-3-yl)pyridin-2-yl) benzamide

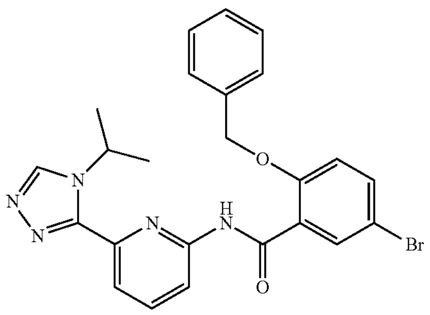 [SMILES: CC(C)n1cnnc1-c1cccc(NC(=O)c2cc(Br)ccc2OCc2ccccc2)n1]

6-(4-Isopropyl-4H-1,2,4-triazol-3-yl)pyridin-2-amine (240 mg, 1.18 mmol) was dissolved in 5 mL of N,N-dimethylformamide, whereupon 2-(benzyloxy)-5-bromobenzoic acid (435 mg, 1.42 mmol), 1-[bis(dimethylamino)methylene]-1H-1,2,3-triazolo[4,5-b]pyridinium 3-oxide hexafluorophosphate (HATU) (897 mg, 2.36 mmol), and N-methylmorpholine (239 mg, 2.36 mmol) were added thereto, and stirring was carried out at 90° C. for 12 hours. 10 mL of distilled water and 10 mL of ethyl acetate were added thereto, and extraction was carried out to obtain an organic layer. The obtained organic layer was washed with 20 mL of a saturated aqueous ammonium chloride solution two times, dried over anhydrous magnesium sulfate, filtered, and concentrated under reduced pressure. The residue was centrifugally separated by mPLC (dichloromethane:methanol=20:1) to obtain 200 mg of 2-(benzyloxy)-5-bromo-N-(6-(4-isopropyl-4H-1,2,4-triazol-3-yl)pyridin-2-yl) benzamide as a product.

$^1$H NMR (400 MHz, $CDCl_3$) δ 9.87 (br s, 1H), 8.43 (d, J=8.8 Hz 1H), 8.30 (s, 1H), 7.93 (t, 3H), 7.82 (d, J=7.6 Hz 1H), 7.54-7.57 (m, 1H), 7.23-7.38 (m, 5H), 6.97 (d, J=8.8 Hz, 1H), 5.29 (s, 1H), 5.18-5.26 (m, 1H), 1.39 (d, J=6.8 Hz, 6H).

Step 1-2) Preparation of 6-bromo-3-(6-(4-isopropyl-4H-1,2,4-triazol-3-yl)pyridin-2-yl)-2,3-dihydro-4H-benzo[e][1,3]oxazin-4-one

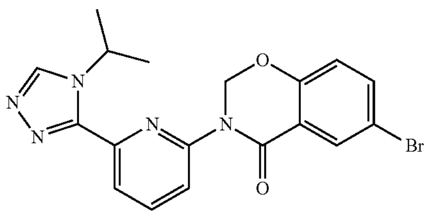 [SMILES: CC(C)n1cnnc1-c1cccc(N2COc3ccc(Br)cc3C2=O)n1]

The 2-(benzyloxy)-5-bromo-N-(6-(4-isopropyl-4H-1,2,4-triazol-3-yl)pyridin-2-yl) benzamide (2.20 g, 4.46 mmol) obtained from the step 1-1) and para-formaldehyde (404 mg, 13.38 mmol) were dissolved in 44 mL of trifluoroacetic acid and stirred at 100° C. for 24 hours. The resulting product was cooled to room temperature and then concentrated under reduced pressure. The residue was centrifugally separated by mPLC (dichloromethane:methanol=20:1) to obtain 620 mg of 6-bromo-3-(6-(4-isopropyl-4H-1,2,4-triazol-3-yl)pyridin-2-yl)-2,3-dihydro-4H-benzo[e][1,3]oxazin-4-one as the title compound.

$^1$H NMR (400 MHz, DMSO-$d_6$) δ 8.92 (s, 1H), 8.11-8.03 (m, 4H), 7.80-7.83 (m, 2H), 7.20 (d, J=8.8 Hz 1H), 6.04 (s, 2H), 5.26-5.31 (m, 1H), 1.49 (d, J=6.8 Hz, 6H).

Step 1-3) Preparation of 6-(1-(cyclopropylmethyl)-1H-pyrazol-4-yl)-3-(6-(4-isopropyl-4H-1,2,4-triazol-3-yl)pyridin-2-yl)-2,3-dihydro-4H-benzo[e][1,3]oxazin-4-one

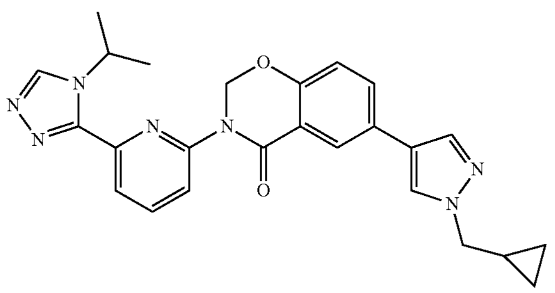 [SMILES: CC(C)n1cnnc1-c1cccc(N2COc3ccc(-c4cnn(CC5CC5)c4)cc3C2=O)n1]

3 mL of dioxane and 1 mL of distilled water were added to the 6-bromo-3-(6-(4-isopropyl-4H-1,2,4-triazol-3-yl) pyridin-2-yl)-2,3-dihydro-4H-benzo[e][1,3]oxazin-4-one (100 mg, 0.241 mmol) obtained from the step 1-2). Then, (1-(cyclopropylmethyl)-1H-pyrazol-4-yl) boronic acid (60 mg, 0.362 mmol), tetrakis(triphenylphosphine) palladium(0) (27.8 mg, 0.0241 mmol), and potassium carbonate (66.7 mg, 0.482 mmol) were added thereto, and stirring was carried out at 90° C. for 12 hours. After the resulting product was cooled to room temperature, 10 mL of distilled water and 10 mL of ethyl acetate were added thereto, and extraction was carried out to obtain an organic layer. The obtained organic layer was washed with 20 mL of a saturated aqueous ammonium chloride solution two times, dried over anhydrous magnesium sulfate, filtered, and concentrated under reduced pressure. The residue was centrifugally separated by mPLC (dichloromethane:methanol=20:1) to obtain 70 mg of 6-(1-(cyclopropylmethyl)-1H-pyrazol-4-yl)-3-(6-(4-isopropyl-4H-1,2,4-triazol-3-yl)pyridine-2-yl)-2,3-dihydro-4H-benzo[e][1,3]oxazin-4-one as the title compound.

$^1$H NMR (400 MHz, DMSO-$d_6$) δ 8.93 (s, 1H), 8.30 (s, 1H), 8.01-8.11 (m, 4H), 7.86 (s, 1H), 7.84-7.85 (m, 1H), 7.52 (d, J=8.4 Hz, 1H), 6.02 (s, 2H), 5.33-5.40 (m, 1H), 4.00 (br d, J=6.4 Hz, 2H), 1.50 (br d, J=6.8 Hz, 6H), 1.20-0.35 (m, 1H), 0.54-0.55 (m, 1H), 0.39-0.40 (m, 1H);

MS(ESI+) m/z 456 $(M+H)^+$.

Preparation Example 2: Preparation of 6-bromo-3-(6-(4-isopropyl-4H-1,2,4-triazol-3-yl)pyridin-2-yl)-2,3-dihydro-4H-benzo[e][1,3]thiazin-4-one Step 2-1) Preparation of 6-bromopicolinohydrazide

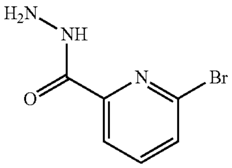

Methyl 6-bromopicolinate (20 g, 92.60 mmol) was dissolved in 20 mL of ethanol, 8.99 mL of hydrazine monohydrate was added thereto, and reflux was carried out at 90° C. for 12 hours. The resulting product was cooled to room temperature and then concentrated under reduced pressure. The residue was provided with ethanol at a volume ratio of ethanol to residue of 10, stirred, filtered, and dried to obtain 19.33 g of 6-bromopicolinohydrazide as a product.

$^1$H NMR (400 MHz, DMSO-$d_6$) δ 9.89 (br s, 1H), 7.86-8.02 (m, 2H), 7.82 (d, J=7.9 Hz, 1H), 4.60 (br d, J=4.0 Hz, 2H).

Step 2-2) Preparation of (E)-N'-(6-bromopicolinoyl)-N,N-dimethylformohydrazonamide

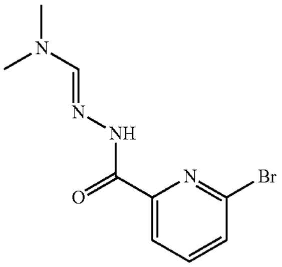

The 6-bromopicolinohydrazide (19.33 g, 5.24 mmol) obtained from the step 2-1) was dissolved in 57 mL of N,N-dimethylformamide, 78 mL of dimethylformamide dimethyl acetal was added thereto, and stirring was carried out at 100° C. for 12 hours. The resulting product was cooled to room temperature and then concentrated under reduced pressure. The residue was provided with methyl tert-butyl ether at a volume ratio of methyl tert-butyl ether to residue of 10 and ethyl acetate at a volume ratio of ethyl acetate to residue of 5, stirred, and then filtered. The resulting product was washed and dried by a mixed solution of methyl (tert-butyl ether):(ethyl acetate)=2:1 to obtain 13.45 g of (E)-N'-(6-bromopicolinoyl)-N,N-dimethylformohydrazonamide as a product.

$^1$H NMR (400 MHz, DMSO-$d_6$) δ 10.78 (s, 1H), 8.07 (s, 1H), 7.95-8.02 (m, 1H), 7.91 (t, J=7.7 Hz, 1H), 7.81 (d, J=7.3 Hz, 1H), 2.83 (s, 6H).

Step 2-3) Preparation of 2-bromo-6-(4-isopropyl-4H-1,2,4-triazol-3-yl)pyridine

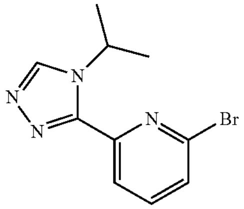

The (E)-N'-(6-bromopicolinoyl)-N,N-dimethylformohydrazonamide (13.45 g, 49.61 mmol) obtained from the step 2-2) was dissolved in 17 mL of acetic acid and 68 mL of acetonitrile, isopropyl amine was added thereto, and reflux was carried out at 80° C. for 12 hours. The resulting product was cooled to room temperature and then filtered while adjusting pH to 8 using a 1 N sodium hydroxide aqueous solution. The resulting product was washed and dried by distilled water to obtain 8 g of 2-bromo-6-(4-isopropyl-4H-1,2,4-triazol-3-yl)pyridine as a product.

$^1$H NMR (400 MHz, DMSO-$d_6$) δ 8.93 (s, 1H), 8.15 (d, J=7.7 Hz, 1H), 7.95 (t, J=7.9 Hz, 1H), 7.79 (d, J=8.1 Hz, 1H), 5.21-5.41 (m, 1H), 1.49 (d, J=6.6 Hz, 5H).

Step 2-4) Preparation of 6-bromo-3-(6-(4-isopropyl-4H-1,2,4-triazol-3-yl)pyridin-2-yl)-2,3-dihydro-4H-benzo[e][1,3]thiazin-4-one

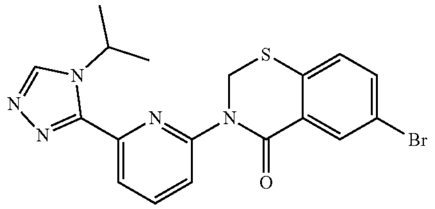 [SMILES: CC(C)n1cnnc1-c1cccc(N2CSc3ccc(Br)cc3C2=O)n1]

The 2-bromo-6-(4-isopropyl-4H-1,2,4-triazol-3-yl)pyridine (1 g, 3.8 mmol) obtained from the step 2-3) was dissolved in 10 mL of toluene, whereupon 6-bromo-2,3-dihydro-1,3-benzothiazin-4-one (1.4 g, 5.7 mmol), tris (dibenzylideneacetone) dipalladium(0) (0.4 g, 0.4 mmol), cesium carbonate (2.2 g, 6.7 mmol), and 4,5-bis(diphenylphosphino)-9,9-dimethylxanthine (0.4 g, 0.6 mmol) were added thereto, and reflux was carried out at 90° C. for 12 hours. After the resulting product was cooled to room temperature, distilled water and dichloromethane were added thereto, and extraction was carried out to obtain an organic layer. The obtained organic layer was concentrated under reduced pressure. The residue was provided with acetonitrile at a volume ratio of acetonitrile to residue of 5, stirred, filtered, and then dried to obtain 800 mg of 6-bromo-3-(6-(4-isopropyl-4H-1,2,4-triazol-3-yl)pyridin-2-yl)-2,3-dihydro-4H-benzo[e][1,3]thiazin-4-one as the title compound.

$^1$H NMR (400 MHz, DMSO-$d_6$) δ 8.88-8.98 (m, 1H), 8.18 (br d, J=2.2 Hz, 1H), 8.03-8.11 (m, 1H), 7.99 (br d, J=7.7 Hz, 1H), 7.86-7.94 (m, 1H), 7.71-7.80 (m, 1H), 7.52 (br d, J=8.2 Hz, 1H), 5.42-5.62 (m, 2H), 5.24-5.42 (m, 1H), 1.49 (br d, J=6.8 Hz, 6H).

Step 2-5) Preparation of 6-(1-(cyclopropylmethyl)-1H-pyrazol-4-yl)-3-(6-(4-isopropyl-4H-1,2,4-triazol-3-yl)pyridin-2-yl)-2,3-dihydro-4H-benzo[e][1,3]thiazin-4-one

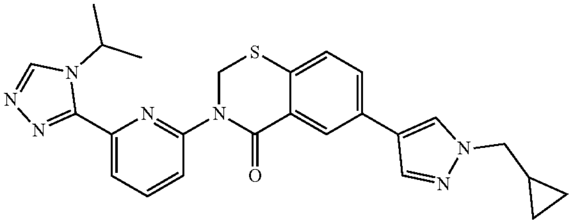 [SMILES: CC(C)n1cnnc1-c1cccc(N2CSc3ccc(-c4cnn(CC5CC5)c4)cc3C2=O)n1]

2 mL of a mixed solution of N,N-dimethylformamide: (distilled water)=4:1 was added to the 6-bromo-3-(6-(4-isopropyl-4H-1,2,4-triazol-3-yl)pyridin-2-yl)-2,3-dihydro-4H-benzo[e][1,3]thiazin-4-one obtained from the step 2-4). Then, (1-(cyclopropylmethyl)-1H-pyrazol-4-yl) boronic acid (58 mg, 0.349 mmol), tetrakis(triphenylphosphine) palladium(0) (27 mg, 0.0232 mmol), and potassium carbonate (48 mg, 0.349 mmol) were added thereto, and stirring was carried out at 90° C. for 12 hours. After the resulting product was cooled to room temperature, 5 mL of distilled water and 10 mL of dichloromethane were added thereto, and extraction was carried out to obtain an organic layer. The obtained organic layer was washed with 10 mL of a saturated aqueous ammonium chloride solution, dried over anhydrous magnesium sulfate, filtered, and concentrated under reduced pressure. The residue was centrifugally separated by mPLC (dichloromethane:methanol=15:1) to obtain 40 mg of 6-(1-(cyclopropylmethyl)-1H-pyrazol-4-yl)-3-(6-(4-isopropyl-4H-1,2,4-triazol-3-yl)pyridin-2-yl)-2,3-dihydro-4H-benzo[e][1,3]thiazin-4-one as the title compound.

$^1$H NMR (400 MHz, DMSO-$d_6$) δ 8.93 (s, 1H), 8.34 (s, 1H), 8.26 (s, 1H), 8.07 (br d, J=7.7 Hz, 1H), 7.89-8.02 (m, 3H), 7.75-7.81 (m, 1H), 7.52 (br d, J=8.8 Hz, 1H), 5.51 (s, 2H), 5.33 (br d, J=6.6 Hz, 1H), 3.99 (br d, J=6.4 Hz, 2H), 1.50 (br d, J=6.4 Hz, 6H), 0.50-0.58 (m, 2H), 0.40 (br d, J=3.7 Hz, 2H);

MS(ESI+) m/z 472 $(M+H)^+$.

Example 1: Preparation of 6-(1-(cyclopropylmethyl)-1H-pyrazol-4-yl)-3-(6-(4-isopropyl-4H-1,2,4-triazol-3-yl)pyridin-2-yl)-2,3-dihydro-4H-benzo[e][1,3]oxazin-4-one

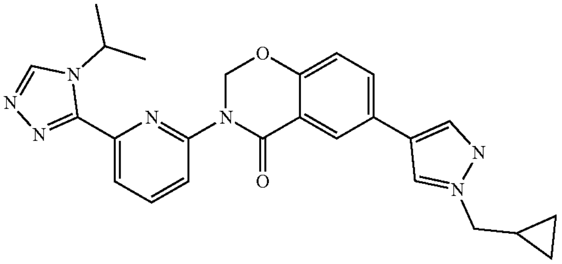

The above compound was obtained in the same manner as in Preparation Example 1.

$^1$H NMR (400 MHz, DMSO-$d_6$) δ 8.93 (s, 1H), 8.30 (s, 1H), 8.01-8.11 (m, 4H), 7.86 (s, 1H), 7.84-7.85 (m, 1H), 7.52 (d, J=8.4 Hz, 1H), 6.02 (s, 2H), 5.33-5.40 (m, 1H), 4.00 (br d, J=6.4 Hz, 2H), 1.50 (br d, J=6.8 Hz, 6H), 1.20-0.35 (m, 1H), 0.54-0.55 (m, 1H), 0.39-0.40 (m, 1H);

MS(ESI+) m/z 456 $(M+H)^+$.

Example 2: Preparation of 3-(6-(4-isopropyl-4H-1,2,4-triazol-3-yl)pyridin-2-yl)-6-(4-(methylsulfonyl)phenyl)-2,3-dihydro-4H-benzo[e][1,3]oxazin-4-one

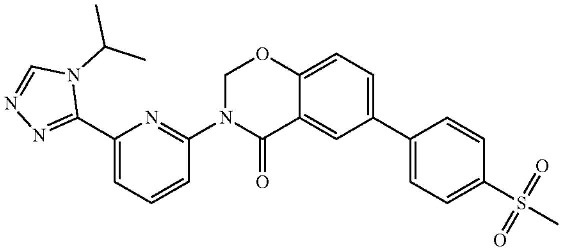 [SMILES: CC(C)n1cnnc1-c1cccc(N2COc3ccc(-c4ccc(S(C)(=O)=O)cc4)cc3C2=O)n1]

The above compound was obtained in the same manner as in Preparation Example 1.

$^1$H NMR (400 MHz, DMSO-$d_6$) δ 8.93 (s, 1H), 8.30 (d, J=2.4 Hz, 1H), 7.98-8.13 (m, 8H), 7.37 (d, J=8.6 Hz, 1H), 6.10 (s, 2H), 5.26-5.37 (m, 1H), 3.27 (s, 3H), 1.51 (d, J=6.8 Hz, 6H);

MS(ESI+) m/z 490 $(M+H)^+$.

Example 3: Preparation of 3-(6-(4-isopropyl-4H-1,2,4-triazol-3-yl)pyridin-2-yl)-6-(pyridin-4-yl)-2,3-dihydro-4H-benzo[e][1,3]oxazin-4-one

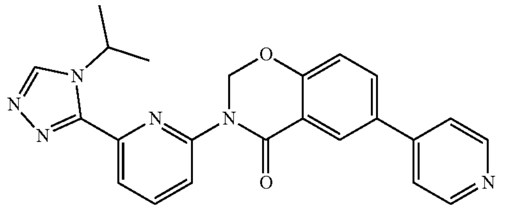 [SMILES: CC(C)n1cnnc1-c1cccc(N2COc3ccc(-c4ccncc4)cc3C2=O)n1]

The above compound was obtained in the same manner as in Preparation Example 1.

$^1$H NMR (400 MHz, DMSO-$d_6$) δ 8.93 (s, 1H), 8.66 (d, J=6.0 Hz, 1H), 8.34 (s, 1H), 8.10-8.15 (m, 2H), 7.95-8.00 (m, 2H), 7.76 (d, J=5.6 Hz 1H), 7.36 (d, J=8.4 Hz, 1H), 6.09 (s, 2H), 5.28-5.35 (m, 1H), 1.50 (d, J=6.6 Hz, 6H);

MS(ESI+) m/z 413 $(M+H)^+$.

Example 4: Preparation of 3-(6-(4-isopropyl-4H-1,2,4-triazol-3-yl)pyridin-2-yl)-6-(4-methylpyrimidin-2-ylamino)-2,3-dihydro-4H-benzo[e][1,3]oxazin-4-one

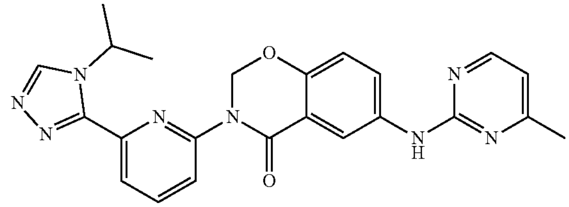 [SMILES: Cc1ccnc(Nc2ccc3c(c2)C(=O)N(c2cccc(-c4nncn4C(C)C)n2)CO3)n1]

The above compound was obtained in the same manner as in Preparation Example 1.

$^1$H NMR (400 MHz, $CDCl_3$) δ 8.40 (s, 1H), 8.28-8.34 (m, 2H), 8.10-8.15 (m, 2H), 7.94 (t, J=8.1 Hz, 1H), 7.86 (dd, J=9.0 Hz, 2.7 Hz, 1H), 7.12 (s, 1H), 7.08 (d, J=9.0 Hz, 1H), 6.65 (d, J=5.1 Hz, 1H), 5.93 (s, 2H), 5.38-5.46 (m, 1H), 2.45 (s, 3H), 1.60 (d, J=1.0 Hz, 6H);

MS(ESI+) m/z 443 $(M+H)^+$.

Example 5: Preparation of 3-(6-(4-isopropyl-4H-1,2,4-triazol-3-yl)pyridin-2-yl)-6-(1-(tetrahydrofuran-3-yl)-1H-pyrazol-4-yl)-2,3-dihydro-4H-benzo[e][1,3]oxazin-4-one

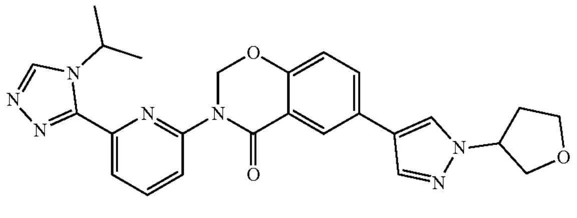 [SMILES: CC(C)n1cnnc1-c1cccc(N2COc3ccc(-c4cnn(C5CCOC5)c4)cc3C2=O)n1]

The above compound was obtained in the same manner as in Preparation Example 1.

$^1$H NMR (400 MHz, $CDCl_3$) δ 8.40 (s, 1H), 8.19 (d, J=2.2 Hz, 1H), 8.12 (dd, J=7.7 Hz, 4.4 Hz, 2H), 7.91-7.98 (m, 1H), 7.81 (d, J=9.1 Hz, 2H), 7.67 (dd, J=8.5 Hz, 2.3 Hz, 1H), 7.09 (d, J=8.6 Hz, 1H), 5.95 (s, 2H), 5.36-5.46 (m, 1H), 4.99-5.08 (m, 1H), 4.14-4.23 (m, 2H), 4.04-4.12 (m, 1H), 3.93-4.02 (m, 1H), 2.47-2.60 (m, 1H), 2.31-2.38 (m, 1H), 1.60 (br d, J=6.8 Hz, 6H);

MS(ESI+) m/z 472 $(M+H)^+$.

Example 6: Preparation of 6-(1-(1-ethoxyethyl)-1H-pyrazol-4-yl)-3-(6-(4-isopropyl-4H-1,2,4-triazol-3-yl)pyridin-2-yl)-2,3-dihydro-4H-benzo[e][1,3]oxazin-4-one

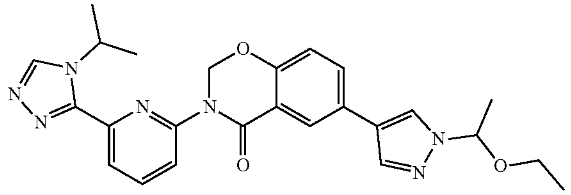 [SMILES: CCOC(C)n1cc(-c2ccc3c(c2)C(=O)N(c2cccc(-c4nncn4C(C)C)n2)CO3)cn1]

The above compound was obtained in the same manner as in Preparation Example 1.

$^1$H NMR (400 MHz, $CDCl_3$) δ 8.40 (s, 1H), 8.22 (d, J=2.2 Hz, 1H), 8.08-8.17 (m, 2H), 7.92-7.99 (m, 1H), 7.91 (s, 1H), 7.82 (s, 1H), 7.69 (dd, J=8.5 Hz, 2.3 Hz, 1H), 7.10 (d, J=8.6 Hz, 1H), 5.96 (s, 2H), 5.56 (q, J=6.0 Hz, 1H), 5.36-5.48 (m, 1H), 3.37-3.56 (m, 2H), 1.73 (d, J=6.0 Hz, 3H), 1.60 (d, J=6.8 Hz, 6H), 1.19 (t, J=7.0 Hz, 3H);

MS(ESI+) m/z 474 $(M+H)^+$.

Example 7: Preparation of 6-(1-(difluoromethyl)-1H-pyrazol-4-yl)-3-(6-(4-isopropyl-4H-1,2,4-triazol-3-yl)pyridin-2-yl)-2,3-dihydro-4H-benzo[e][1,3]oxazin-4-one

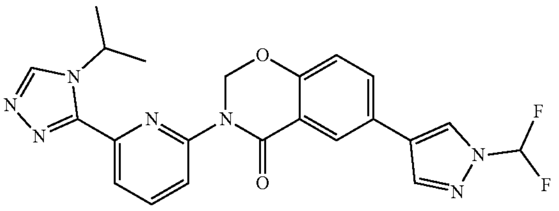 [SMILES: CC(C)n1cnnc1-c1cccc(N2COc3ccc(-c4cnn(C(F)F)c4)cc3C2=O)n1]

The above compound was obtained in the same manner as in Preparation Example 1.

$^1$H NMR (400 MHz, $CDCl_3$) δ 8.39 (s, 1H), 8.23-8.26 (m, 1H), 8.09-8.14 (m, 3H), 7.93-7.98 (m, 2H), 7.67-7.72 (m, 1H), 7.11-7.17 (m, 1H), 5.96 (s, 2H), 5.36-5.44 (m, 1H), 1.59 (d, J=1.0 Hz, 6H);

MS(ESI+) m/z 452 $(M+H)^+$.

Example 8: Preparation of 6-(1-cyclopropyl-1H-pyrazol-4-yl)-3-(6-(4-isopropyl-4H-1,2,4-triazol-3-yl)pyridin-2-yl)-2,3-dihydro-4H-benzo[e][1,3]oxazin-4-one

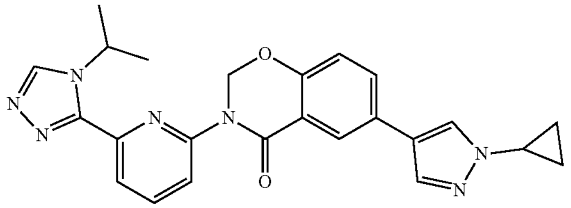

The above compound was obtained in the same manner as in Preparation Example 1.

$^1$H NMR (400 MHz, $CDCl_3$) δ 8.93 (s, 1H), 8.34 (s, 1H), 8.04-8.13 (m, 2H), 7.99 (br d, J=7.3 Hz, 2H), 7.91 (s, 1H), 7.86 (dd, J=8.6 Hz, 2.0 Hz, 1H), 7.17-7.23 (m, 1H), 6.02 (s, 2H), 5.26-5.37 (m, 1H), 3.70-3.79 (m, 1H), 1.50 (d, J=6.6 Hz, 6H), 1.05-1.12 (m, 2H), 0.94-1.01 (m, 2H);

MS(ESI+) m/z 442 $(M+H)^+$.

Example 9: Preparation of 6-(1-isobutyl-1H-pyrazol-4-yl)-3-(6-(4-isopropyl-4H-1,2,4-triazol-3-yl)pyridin-2-yl)-2,3-dihydro-4H-benzo[e][1,3]oxazin-4-one

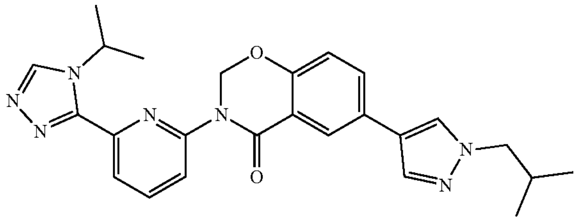 [SMILES: CC(C)Cn1cc(-c2ccc3c(c2)C(=O)N(c2cccc(-c4nncn4C(C)C)n2)CO3)cn1]

The above compound was obtained in the same manner as in Preparation Example 1.

$^1$H NMR (400 MHz, $CDCl_3$) δ 8.41 (s, 1H), 8.19 (d, J=2.2 Hz, 1H), 8.12 (dd, J=8.1 Hz, 3.5 Hz, 2H), 7.96 (d, J=7.9 Hz, 1H), 7.81 (s, 1H), 7.64-7.72 (m, 2H), 7.09 (d, J=8.6 Hz, 1H), 5.95 (s, 2H), 5.36-5.49 (m, 1H), 3.97 (d, J=7.3 Hz, 2H), 2.26 (m, 1H), 1.60 (d, J=6.8 Hz, 6H), 0.96 (d, J=6.6 Hz, 6H);

MS(ESI+) m/z 458 $(M+H)^+$.

Example 10: Preparation of 6-(4-(difluoromethyl)pyrimidin-2-ylamino)-3-(6-(4-isopropyl-4H-1,2,4-triazol-3-yl)pyridin-2-yl)-2,3-dihydro-4H-benzo[e][1,3]oxazin-4-one

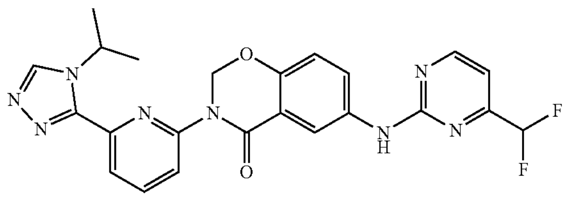 [SMILES: CC(C)n1cnnc1-c1cccc(N2COc3ccc(Nc4nccc(C(F)F)n4)cc3C2=O)n1]

The above compound was obtained in the same manner as in Preparation Example 1.

$^1$H NMR (400 MHz, $CDCl_3$) δ 8.62 (d, J=4.8 Hz, 1H), 8.40 (s, 1H), 8.30 (d, J=2.7 Hz, 1H), 8.13 (dd, J=7.5 Hz, 2.7 Hz, 2H), 7.95 (t, J=8.0 Hz, 1H), 7.86 (dd, J=8.8 Hz, 2.7 Hz, 1H), 7.11 (d, J=8.8 Hz, 1H), 7.05 (d, J=4.9 Hz, 1H), 5.94 (s, 2H), 5.29-5.47 (m, 1H), 1.61 (d, J=7.0 Hz, 6H);

MS(ESI+) m/z 479 $(M+H)^+$.

Example 11: Preparation of 6-(1-isopentyl-1H-pyrazol-4-yl)-3-(6-(4-isopropyl-4H-1,2,4-triazol-3-yl)pyridin-2-yl)-2,3-dihydro-4H-benzo[e][1,3]oxazin-4-one

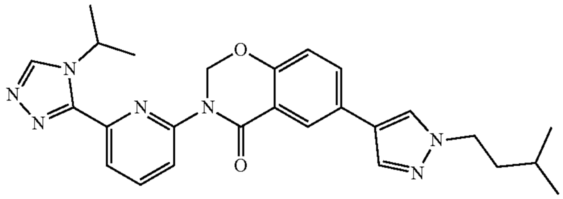 [SMILES: CC(C)CCn1cc(-c2ccc3c(c2)C(=O)N(c2cccc(-c4nncn4C(C)C)n2)CO3)cn1]

The above compound was obtained in the same manner as in Preparation Example 1.

$^1$H NMR (400 MHz, $CDCl_3$) δ 8.43 (s, 1H), 8.15-8.20 (m, 1H), 8.08-8.15 (m, 2H), 7.87-8.03 (m, 1H), 7.79 (s, 1H), 7.63-7.72 (m, 2H), 7.08 (d, J=8.4 Hz, 1H), 5.94 (s, 2H), 5.36-5.48 (m, 1H), 4.19 (t, J=7.4 Hz, 2H), 1.82 (q, J=7.3 Hz, 2H), 1.60 (br d, J=6.6 Hz, 6H), 0.98 (d, J=6.6 Hz, 6H);

MS(ESI+) m/z 472 $(M+H)^+$.

Example 12: Preparation of 1-(4-(3-(6-(4-isopropyl-4H-1,2,4-triazol-3-yl)pyridin-2-yl)-4-oxo-3,4-dihydro-2H-benzo[e][1,3]oxazin-6-yl)phenyl) cyclopropanecarbonitrile

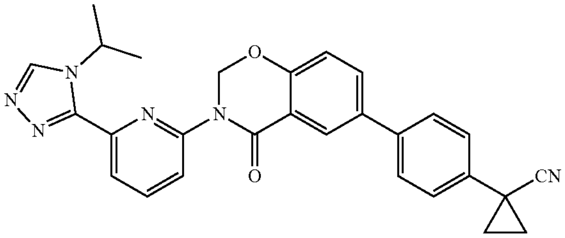 [SMILES: CC(C)n1cnnc1-c1cccc(N2COc3ccc(-c4ccc(C5(C#N)CC5)cc4)cc3C2=O)n1]

The above compound was obtained in the same manner as in Preparation Example 1.

$^1$H NMR (400 MHz, $CDCl_3$) δ 8.41 (s, 1H), 8.28-8.36 (m, 1H), 8.13 (br dd, J=7.6 Hz, 4.1 Hz, 2H), 7.96 (t, J=8.0 Hz, 1H), 7.77 (dd, J=8.5 Hz, 2.1 Hz, 1H), 7.56-7.66 (m, J=8.2 Hz, 2H), 7.34-7.45 (m, J=8.2 Hz, 2H), 7.10-7.26 (m, 1H), 5.98 (s, 2H), 5.36-5.47 (m, 1H), 1.77-1.83 (m, 2H), 1.61 (br d, J=6.8 Hz, 6H), 1.45-1.51 (m, 2H);

MS(ESI+) m/z 477 $(M+H)^+$.

Example 13: Preparation of 6-(4-((1H-pyrazol-1-yl) methyl) phenyl)-3-(6-(4-isopropyl-4H-1,2,4-triazol-3-yl)pyridin-2-yl)-2,3-dihydro-4H-benzo[e][1,3] oxazin-4-one

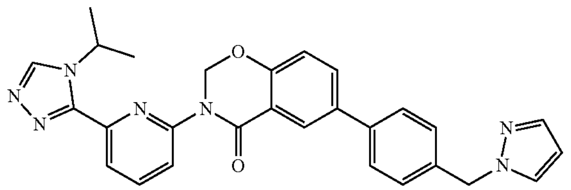 [SMILES: CC(C)n1cnnc1-c1cccc(N2COc3ccc(-c4ccc(Cn5cccn5)cc4)cc3C2=O)n1]

The above compound was obtained in the same manner as in Preparation Example 1.

$^1$H NMR (400 MHz, $CDCl_3$) δ 8.40 (s, 1H), 8.32 (d, J=2.4 Hz, 1H), 8.10-8.17 (m, 2H), 7.93-7.98 (m, 1H), 7.76 (dd, J=8.6 Hz, 2.4 Hz, 1H), 7.59-7.61 (m, 3H), 7.46 (d, J=1.8 Hz, 1H), 7.32 (d, J=8.4 Hz, 2H), 7.16 (d, J=8.6 Hz, 1H), 6.32-6.34 (m, 1H), 5.98 (s, 2H), 5.39-5.46 (m, 3H), 1.60 (d, J=1.0 Hz, 6H);

MS(ESI+) m/z 492 $(M+H)^+$.

Example 14: Preparation of 6-(1-(cyclopropylmethyl)-1H-pyrazol-4-yl)-3-(6-(4-isopropyl-4H-1,2,4-triazol-3-yl)pyridin-2-yl)-7-methyl-2,3-dihydro-4H-benzo[e][1,3]oxazin-4-one

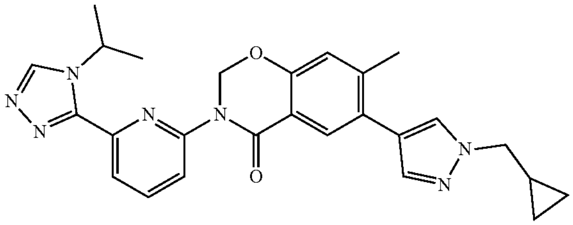 [SMILES: Cc1cc2c(cc1-c1cnn(CC3CC3)c1)C(=O)N(c1cccc(-c3nncn3C(C)C)n1)CO2]

The above compound was obtained in the same manner as in Preparation Example 1.

$^1$H NMR (400 MHz, $CDCl_3$) δ 8.38-8.40 (m, 1H), 8.08-8.12 (m, 2H), 8.03 (s, 1H), 7.90-7.95 (m, 1H), 7.65 (d, J=2.2 Hz, 2H), 6.97 (s, 1H), 5.93 (s, 2H), 5.37-5.50 (m, 2H), 4.06 (d, J=7.1 Hz, 2H), 2.47 (s, 3H), 1.59 (d, J=6.6 Hz, 6H), 0.68-0.74 (m, 2H), 0.43 (d, J=5.7 Hz, 2H);

MS(ESI+) m/z 470 $(M+H)^+$.

Example 15: Preparation of 6-(1-isopropyl-1H-pyrazol-4-yl)-3-(6-(4-isopropyl-4H-1,2,4-triazol-3-yl)pyridin-2-yl)-7-methyl-2,3-dihydro-4H-benzo[e][1,3]oxazin-4-one

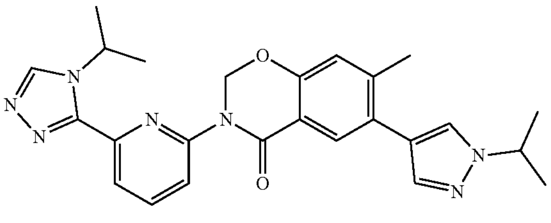 [SMILES: Cc1cc2c(cc1-c1cnn(C(C)C)c1)C(=O)N(c1cccc(-c3nncn3C(C)C)n1)CO2]

The above compound was obtained in the same manner as in Preparation Example 1.

$^1$H NMR (400 MHz, $CDCl_3$) δ 8.37-8.41 (m, 1H), 8.07-8.12 (m, 2H), 7.98-8.04 (m, 1H), 7.90-7.96 (m, 1H), 7.65 (s, 1H), 7.56 (s, 1H), 6.97 (s, 1H), 5.93 (s, 2H), 5.36-5.51 (m, 2H), 2.47 (s, 3H), 1.57-1.61 (m, 12H);

MS(ESI+) m/z 458 $(M+H)^+$.

Example 16: Preparation of 3-(6-(4-isopropyl-4H-1,2,4-triazol-3-yl)pyridin-2-yl)-7-methyl-6-(pyrimidin-5-yl)-2,3-dihydro-4H-benzo[e][1,3]oxazin-4-one

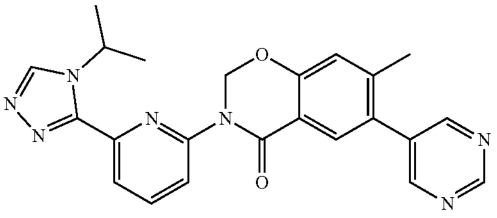 [SMILES: Cc1cc2c(cc1-c1cncnc1)C(=O)N(c1cccc(-c3nncn3C(C)C)n1)CO2]

The above compound was obtained in the same manner as in Preparation Example 1.

$^1$H NMR (400 MHz, $CDCl_3$) δ 9.25 (s, 1H), 9.00 (s, 1H), 8.75 (s, 2H), 8.39 (s, 1H), 8.09 (t, J=8.8 Hz, 2H), 7.89-7.97 (m, 2H), 7.06 (s, 1H), 5.97 (s, 2H), 5.34-5.43 (m, 1H), 2.35 (s, 3H), 1.59 (d, J=6.8 Hz, 6H);

MS(ESI+) m/z 428 $(M+H)^+$.

Example 17: Preparation of 3-(6-(4-isopropyl-4H-1,2,4-triazol-3-yl)pyridin-2-yl)-7-methyl-6-(2-(methylthio)pyrimidin-5-yl)-2,3-dihydro-4H-benzo[e][1,3] oxazin-4-one

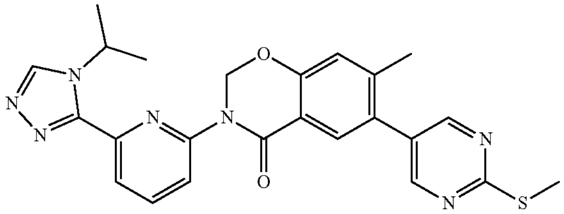 [SMILES: CSc1ncc(-c2cc3c(cc2C)OCN(c2cccc(-c4nncn4C(C)C)n2)C3=O)cn1]

The above compound was obtained in the same manner as in Preparation Example 1.

$^1$H NMR (400 MHz, $CDCl_3$) δ 8.54 (s, 2H), 8.36-8.44 (m, 1H), 8.06-8.17 (m, 2H), 7.91-7.97 (m, 2H), 7.03-7.10 (m, 1H), 5.96 (s, 2H), 5.33-5.44 (m, 1H), 2.63 (s, 3H), 2.36 (s, 3H), 1.60 (br d, J=6.6 Hz, 6H);

MS(ESI+) m/z 474 $(M+H)^+$.

Example 18: Preparation of 3-(6-(4-isopropyl-4H-1,2,4-triazol-3-yl)pyridin-2-yl)-7-methyl-6-(1-(tetrahydrofuran-3-yl)-1H-pyrazol-4-yl)-2,3-dihydro-4H-benzo[e][1,3]oxazin-4-one

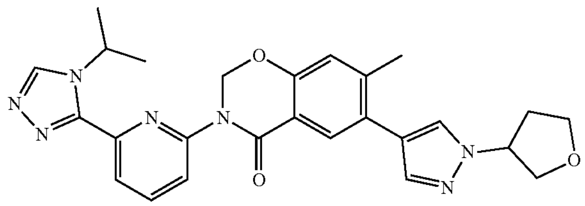 [SMILES: Cc1cc2c(cc1-c1cnn(C3CCOC3)c1)C(=O)N(c1cccc(-c3nncn3C(C)C)n1)CO2]

The above compound was obtained in the same manner as in Preparation Example 1.

$^1$H NMR (400 MHz, $CDCl_3$) δ 8.39 (s, 1H), 8.06-8.13 (m, 2H), 7.99-8.04 (m, 1H), 7.90-7.96 (m, 1H), 7.63 (d, J=16.1 Hz, 2H), 6.92-6.99 (m, 1H), 5.92 (s, 2H), 5.36-5.45 (m, 1H), 5.00-5.10 (m, 1H), 4.14-4.22 (m, 2H), 4.07-4.13 (m, 1H), 3.92-4.01 (m, 1H), 2.49-2.58 (m, 1H), 2.45 (s, 3H), 2.36-2.42 (m, 1H), 1.59 (d, J=6.6 Hz, 6H);

MS(ESI+) m/z 486 $(M+H)^+$.

Example 19: Preparation of 6-(4-cyclopropyl-1H-imidazol-1-yl)-3-(6-(4-isopropyl-4H-1,2,4-triazol-3-yl)pyridin-2-yl)-2,3-dihydro-4H-benzo[e][1,3]oxazin-4-one

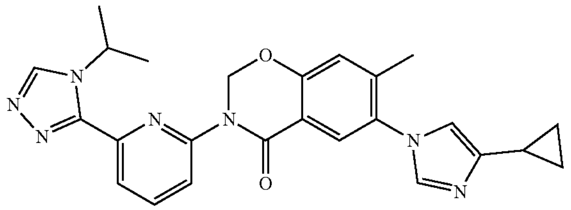 [SMILES: Cc1cc2c(cc1-n1cnc(C3CC3)c1)C(=O)N(c1cccc(-c3nncn3C(C)C)n1)CO2]

The above compound was obtained in the same manner as in Preparation Example 1.

$^1$H NMR (400 MHz, DMSO-$d_6$) δ 8.50 (s, 1H), 7.93-8.12 (m, 4H), 7.76 (s, 1H), 7.57-7.61 (dd, J=2.8 Hz, 2.8 Hz, 1H), 7.21-7.23 (d, J=8.4 Hz, 1H), 7.05 (s, 1H), 5.99 (s, 2H), 5.12-5.40 (m, 1H), 1.76-1.97 (m, 1H), 1.61 (d, J=6.6 Hz, 6H), 0.90-0.95 (m, 2H), 0.75-0.80 (m, 2H);

MS(ESI+) m/z 442 $(M+H)^+$.

Example 20: Preparation of 6-(1-(1-ethoxyethyl)-1H-pyrazol-4-yl)-3-(6-(4-isopropyl-4H-1,2,4-triazol-3-yl)pyridin-2-yl)-7-methyl-2,3-dihydro-4H-benzo[e][1,3]oxazin-4-one

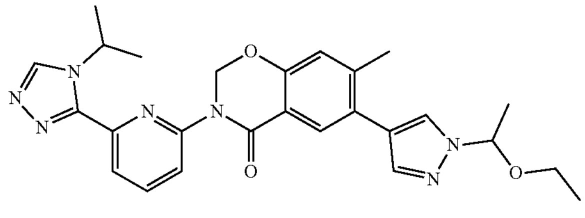 [SMILES: CCOC(C)n1cc(-c2cc3c(cc2C)OCN(c2cccc(-c4nncn4C(C)C)n2)C3=O)cn1]

The above compound was obtained in the same manner as in Preparation Example 1.

$^1$H NMR (400 MHz, $CDCl_3$) δ 8.38-8.41 (m, 1H), 8.10 (dd, J=8.0 Hz, 1.7 Hz, 2H), 8.04 (s, 1H), 7.93 (s, 1H), 7.72 (s, 1H), 7.66 (s, 1H), 6.98 (s, 1H), 5.93 (s, 2H), 5.57 (q, J=6.0 Hz, 1H), 5.39-5.43 (m, 1H), 3.48-3.57 (m, 1H), 3.36-3.46 (m, 1H), 2.46 (s, 3H), 1.74 (d, J=6.0 Hz, 3H), 1.60 (d, J=6.8 Hz, 6H), 1.19 (t, J=7.0 Hz, 3H);

MS(ESI+) m/z 488 $(M+H)^+$.

Example 21: Preparation of 6-(1-(cyclopropylmethyl)-1H-pyrazol-4-yl)-3-(6-(4-isopropyl-4H-1,2,4-triazol-3-yl)pyridin-2-yl)-2,3-dihydro-4H-benzo[e][1,3]thiazin-4-one

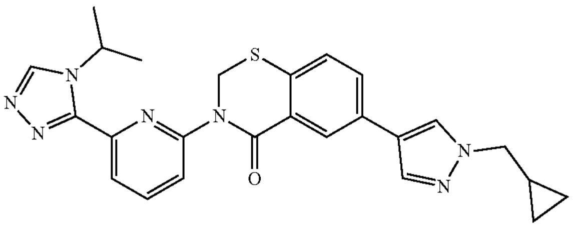 [SMILES: CC(C)n1cnnc1-c1cccc(N2CSc3ccc(-c4cnn(CC5CC5)c4)cc3C2=O)n1]

The above compound was obtained in the same manner as in Preparation Example 2.

$^1$H NMR (400 MHz, DMSO-$d_6$) δ 8.93 (s, 1H), 8.34 (s, 1H), 8.26 (s, 1H), 8.07 (br d, J=7.7 Hz, 1H), 7.89-8.02 (m, 3H), 7.75-7.81 (m, 1H), 7.52 (br d, J=8.8 Hz, 1H), 5.51 (s, 2H), 5.33 (br d, J=6.6 Hz, 1H), 3.99 (br d, J=6.4 Hz, 2H), 1.50 (br d, J=6.4 Hz, 6H), 0.50-0.58 (m, 2H), 0.40 (br d, J=3.7 Hz, 2H);

MS(ESI+) m/z 472 $(M+H)^+$.

Example 22: Preparation of 6-(1-isopropyl-1H-pyrazol-4-yl)-3-(6-(4-isopropyl-4H-1,2,4-triazol-3-yl)pyridin-2-yl)-2,3-dihydro-4H-benzo[e][1,3]thiazin-4-one

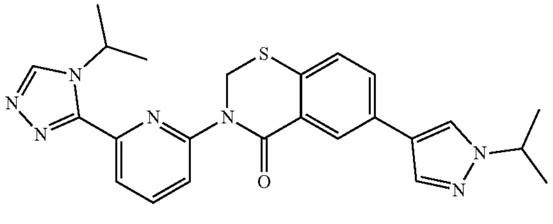 [SMILES: CC(C)n1cc(-c2ccc3c(c2)C(=O)N(c2cccc(-c4nncn4C(C)C)n2)CS3)cn1]

The above compound was obtained in the same manner as in Preparation Example 2.

$^1$H NMR (400 MHz, DMSO-$d_6$) δ 8.93 (s, 1H), 8.34 (s, 1H), 8.26 (s, 1H), 8.07 (br d, J=7.7 Hz, 1H), 7.89-8.02 (m, 3H), 7.75-7.81 (m, 1H), 7.52 (br d, J=8.8 Hz, 1H), 5.51 (s, 2H), 5.33 (br d, J=6.6 Hz, 1H), 3.99 (br d, J=6.4 Hz, 2H), 1.50 (br d, J=6.4 Hz, 6H), 0.50-0.58 (m, 2H), 0.40 (br d, J=3.7 Hz, 2H);

MS(ESI+) m/z 472 $(M+H)^+$.

Example 23: Preparation of 6-(2-cyclopropylpyrimidin-5-yl)-3-(6-(4-isopropyl-4H-1,2,4-triazol-3-yl)pyridin-2-yl)-2,3-dihydro-4H-benzo[e][1,3]thiazin-4-one

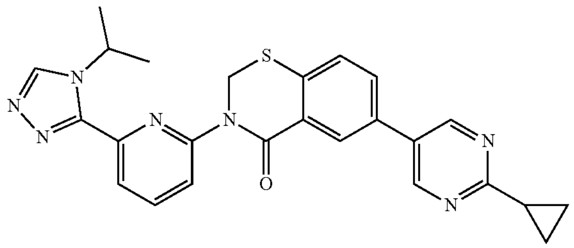 [SMILES: CC(C)n1cnnc1-c1cccc(N2CSc3ccc(-c4cnc(C5CC5)nc4)cc3C2=O)n1]

The above compound was obtained in the same manner as in Preparation Example 2.

$^1$H NMR (400 MHz, DMSO-$d_6$) δ 9.00 (s, 2H), 8.93 (s, 1H), 8.38-8.41 (m, 1H), 8.06-8.11 (m, 1H), 7.98-8.02 (m, 1H), 7.89-7.96 (m, 2H), 7.69 (d, J=8.2 Hz, 1H), 5.55 (s, 2H), 5.29-5.40 (m, 1H), 2.21-2.30 (m, 1H), 1.50 (d, J=6.6 Hz, 6H), 1.04-1.12 (m, 4H);

MS(ESI+) m/z 470 $(M+H)^+$.

Example 24: Preparation of 6-(1-cyclopropyl-1H-pyrazol-4-yl)-3-(6-(4-isopropyl-4H-1,2,4-triazol-3-yl)pyridin-2-yl)-2,3-dihydro-4H-benzo[e][1,3]thiazin-4-one

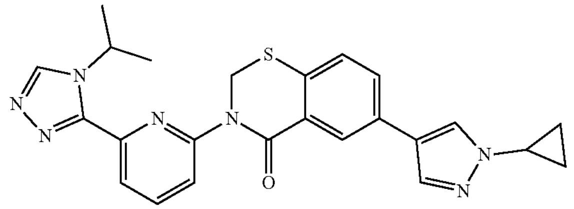 [SMILES: CC(C)n1cnnc1-c1cccc(N2CSc3ccc(-c4cnn(C5CC5)c4)cc3C2=O)n1]

The above compound was obtained in the same manner as in Preparation Example 2.

$^1$H NMR (400 MHz, DMSO-$d_6$) δ 8.93 (s, 1H), 8.37 (s, 1H), 8.26 (d, J=1.6 Hz, 1H), 8.07 (br d, J=8.1 Hz, 1H), 7.98 (d, J=7.7 Hz, 1H), 7.93 (s, 1H), 7.77 (dd, J=7.8 Hz, 1.4 Hz, 1H), 7.49-7.53 (m, 1H), 7.16-7.20 (m, 1H), 5.51 (s, 2H), 5.31-5.37 (m, 1H), 3.76 (br dd, J=7.5 Hz, 3.5 Hz, 1H), 1.50 (d, J=6.8 Hz, 6H), 1.09 (br d, J=3.7 Hz, 2H), 0.98-1.00 (m, 2H);

MS(ESI+) m/z 458 $(M+H)^+$.

Example 25: Preparation of 3-(6-(4-isopropyl-4H-1,2,4-triazol-3-yl)pyridin-2-yl)-6-(2-methylpyrimidin-5-yl)-2,3-dihydro-4H-benzo[e][1,3]thiazin-4-one

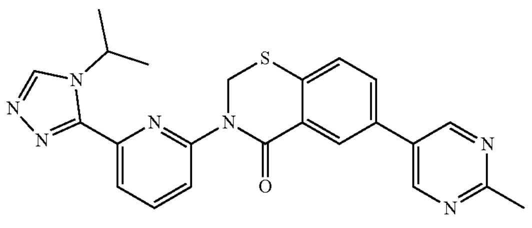 [SMILES: Cc1ncc(-c2ccc3c(c2)C(=O)N(c2cccc(-c4nncn4C(C)C)n2)CS3)cn1]

The above compound was obtained in the same manner as in Preparation Example 2.

$^1$H NMR (400 MHz, DMSO-$d_6$) δ 9.07 (s, 1H), 8.93 (s, 1H), 8.41-8.44 (m, 1H), 8.06-8.11 (m, 1H), 7.97-8.01 (m, 1H), 7.91-7.96 (m, 1H), 7.68-7.72 (m, 1H), 7.33-7.38 (m, 1H), 7.15-7.20 (m, 1H), 5.56 (s, 2H), 5.31-5.37 (m, 1H), 2.68-2.75 (m, 3H), 1.51 (br d, J=6.8 Hz, 6H);

MS(ESI+) m/z 444 $(M+H)^+$.

Experimental Example 1: Assay of Inhibitory Ability Against ASK-1 Enzyme Activity (ADP-Glo™ Kinase Assay)

In order to evaluate the inhibitory ability of the compounds of Examples 1 to 25 against ASK-1 enzyme activity, the following experiment was carried out using ADP-Glo™ (Promega, Cat. No. V9101). Each of the compounds was prepared into a solution at concentrations of 0.32 nM, 1.6 nM, 8 nM, 40 nM, 200 nM, 1,000 nM by adding a kinase buffer solution (40 mM Tris, 20 mM $MgCl_2$, 0.1 mg/mL bovine serum albumin in $H_2O$). Subsequently, 250 μM of ATP (Promega, Cat. No. V915A) and 0.5 g/L of MBP substrate (Signal Chem, Cat. No. 42-51N) were added thereto, and the mixture was reacted at 30° C. for 40 minutes in the presence of 15 ng of ASK-1 enzyme (Signal Chem, Cat. No. M13-11G-10). Then, the ADP-Glo™ reagent and a kinase detection reagent were sequentially added thereto and reacted for 40 minutes and 10 minutes, respectively. After completion of the reaction, luminescence was measured using a Synergy™ NEO microplate reader (BioTEK, NEOB-1311189).

The inhibitory ability of the compounds of Examples 1 to 25 against ASK-1 enzyme activity was verified by analyzing data from the measured RLU values. Specifically, the inhibitory ability against ASK-1 enzyme activity was assessed by deriving the residual activity percentage of the ASK-1 enzyme in the samples treated with the compounds at the concentration to be tested, while using the RLU value of the sample not treated with the compounds as a 100% control. The $IC_{50}$ value (nM) of the ASK-1 inhibitor was determined as the concentration of the compounds at which the inhibition of ASK-1 enzyme activity was induced by 50% compared to the control, and the results are shown in Table 1 below. As shown in Table 1, all of the compounds of Examples 1 to 25 showed excellent inhibitory activity against ASK-1 with the $IC_{50}$ values of 100 nM or below.

TABLE 1

| | ASK-1 $IC_{50}$ (nM) |
|---|---|
| Example 1 | 9.3 |
| Example 2 | 50.0 |
| Example 3 | 9.1 |
| Example 4 | 7.8 |
| Example 5 | 38.8 |
| Example 6 | 29.2 |
| Example 7 | 33.1 |
| Example 8 | 13.8 |
| Example 9 | 11.0 |
| Example 10 | 7.2 |
| Example 11 | 18.5 |
| Example 12 | 17.0 |
| Example 13 | 46.4 |
| Example 14 | 4.4 |
| Example 15 | 4.5 |
| Example 16 | 20.0 |
| Example 17 | 7.8 |
| Example 18 | 10.6 |
| Example 19 | 4.0 |

TABLE 1-continued

| | ASK-1 $IC_{50}$ (nM) |
|---|---|
| Example 20 | 3.6 |
| Example 21 | 7.3 |
| Example 22 | 6.1 |
| Example 23 | 23.1 |
| Example 24 | 26.2 |
| Example 25 | 76.8 |

The invention claimed is:

1. A compound selected from the group consisting of:

3-(6-(4-isopropyl-4H-1,2,4-triazol-3-yl)pyridin-2-yl)-6-(4-(methylsulfonyl) phenyl)-2,3-dihydro-4H-benzo [e][1,3]oxazin-4-one, 3-(6-(4-isopropyl-4H-1,2,4-triazol-3-yl)pyridin-2-yl)-6-(pyridin-4-yl)-2,3-dihydro-4H-benzo[e][1,3]oxazin-4-one, 3-(6-(4-isopropyl-4H-1,2,4-triazol-3-yl)pyridin-2-yl)-6-(4-methylpyrimidin-2-ylamino)-2,3-dihydro-4H-benzo[e][1,3]oxazin-4-one, 3-(6-(4-isopropyl-4H-1,2,4-triazol-3-yl)pyridin-2-yl)-6-(1-(tetrahydrofuran-3-yl)-1H-pyrazol-4-yl)-2,3-dihydro-4H-benzo[e][1,3]oxazin-4-one, 6-(1-(1-ethoxyethyl)-1H-pyrazol-4-yl)-3-(6-(4-isopropyl-4H-1,2,4-triazol-3-yl)pyridin-2-yl)-2,3-dihydro-4H-benzo[e][1,3]oxazin-4-one, 6-(1-isopentyl-1H-pyrazol-4-yl)-3-(6-(4-isopropyl-4H-1,2,4-triazol-3-yl) pyridin-2-yl)-2,3-dihydro-4H-benzo[e][1,3]oxazin-4-one, 1-(4-(3-(6-(4-isopropyl-4H-1,2,4-triazol-3-yl)pyridin-2-yl)-4-oxo-3,4-dihydro-2H-benzo [e][1,3]oxazin-6-yl) phenyl)cyclopropanecarbonitrile, 6-(4-((1H-pyrazol-1-yl) methyl)phenyl)-3-(6-(4-isopropyl-4H-1,2,4-triazol-3-yl)pyridin-2-yl)-2,3-dihydro-4H-benzo[e][1,3]oxazin-4-one, 6-(1-(cyclopropylmethyl)-1H-pyrazol-4-yl)-3-(6-(4-isopropyl-4H-1,2,4-triazol-3-yl)pyridin-2-yl)-7-methyl-2,3-dihydro-4H-benzo[e][1,3]oxazin-4-one, 3-(6-(4-isopropyl-4H-1,2,4-triazol-3-yl)pyridin-2-yl)-7-methyl-6-(pyrimidin-5-yl)-2,3-dihydro-4H-benzo [e][1,3]oxazin-4-one, 3-(6-(4-isopropyl-4H-1,2,4-triazol-3-yl) pyridin-2-yl)-7-methyl-6-(2-(methylthio)pyrimidin-5-yl)-2,3-dihydro-4H-benzo[e][1,3]oxazin-4-one, 3-(6-(4-isopropyl-4H-1,2,4-triazol-3-yl) pyridin-2-yl)-7-methyl-6-(1-(tetrahydrofuran-3-yl)-1H- pyrazol-4-yl)-2,3-dihydro-4H-benzo[e][1,3]oxazin-4-one, and 6-(1-(1-ethoxyethyl)-1H-pyrazol-4-yl)-3-(6-(4-isopropyl-4H-1,2,4-triazol-3-yl) pyridin-2-yl)-7- methyl-2,3-dihydro-4H-benzo[e][1,3]oxazin-4-one, or a pharmaceutically acceptable salt thereof.

2. A method for preparing the compound or the pharmaceutically acceptable salt thereof according to claim 1, comprising:

reacting a compound of Chemical Formula 2 with $R_3$-boronic acid or an $R_3$-halogen compound:

[Chemical Formula 2]

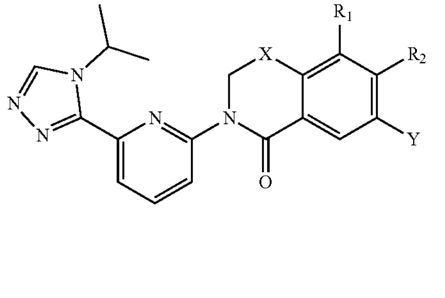

in which

X is O;

Y is halogen or amine;

$R_1$ is H;

$R_2$ is H or CH; and

R3 is substituted or unsubstituted phenyl, pyrazolyl, pyridinyl, pyrimidinyl, or pyrimidinylamino, wherein the compound of Chemical Formula 2 is prepared by:

(a-1) reacting 6-(4-isopropyl-4H-1,2,4-triazol-3-yl)pyridin-2-amine with 2-(benzyloxy)-3-$R_1$-4-$R_2$-5-Y-benzoic acid to obtain a compound of Chemical Formula 3:

[Chemical Formula 3]

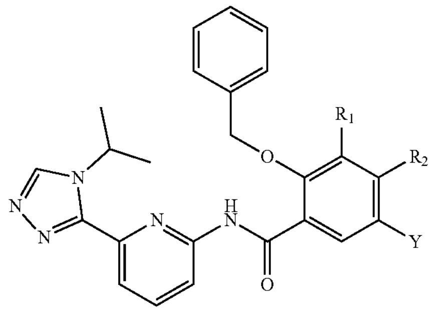

in which:

Y is halogen or nitro;

$R_1$ is H; and $R_2$ is H or CH, and (a-2) reacting the compound of Chemical Formula 3 with para-formaldehyde to cyclize to obtain the compound of Chemical Formula 2.

3. The method of claim 2, wherein the method is performed by a coupling reaction with a palladium catalyst.

4. The method of claim 2, wherein (a-1) is performed in the presence of 1-[bis(dimethylamino)methylene]-1H-1,2,3-triazolo[4,5-b]pyridinium 3-oxide hexafluorophosphate (HATU) and a base.

5. A pharmaceutical composition for preventing or treating an ASK-1 mediated disease, the composition comprising: the compound or the pharmaceutically acceptable salt thereof according to claim 1, as an active ingredient.

6. The pharmaceutical composition of claim 5, wherein composition further comprises a pharmaceutically acceptable carrier.

7. A method for treating an ASK-1 mediated disease in a subject in need thereof, the method comprising administering the pharmaceutical composition according to claim 5 to the subject, wherein the ASK-1 mediated disease is selected from the group consisting of diabetes, diabetic nephropathy, kidney disease, kidney fibrosis, lung fibrosis, idiopathic pulmonary fibrosis (IPF), liver fibrosis, pulmonary hypertension, chronic obstructive pulmonary disease (COPD), acute lung injury, nonalcoholic steatohepatitis, liver disease, alcoholic liver disease, alcoholic hepatitis, autoimmune disease, cancer, transplantation rejection, congenital cartilage malformation, and a combination thereof.

8. The method of claim 7, wherein the ASK-1 mediated disease is selected from the group consisting of diabetes, diabetic nephropathy, kidney disease, kidney fibrosis, lung fibrosis, idiopathic pulmonary fibrosis (IPF), pulmonary hypertension, chronic obstructive pulmonary disease (COPD), acute lung injury, transplantation rejection, a disease congenital cartilage malformation, and a combination thereof.

9. The compound or the pharmaceutically acceptable salt thereof according to claim 1, wherein the compound is selected from the group consisting of:

3-(6-(4-isopropyl-4H-1,2,4-triazol-3-yl)pyridin-2-yl)-6-(pyridin-4-yl)-2,3-dihydro-4H-benzo[e][1,3]oxazin-4-one, 3-(6-(4-isopropyl-4H-1,2,4-triazol-3-yl)pyridin-2-yl)-6-(4-methylpyrimidin-2-ylamino)-2,3-dihydro-4H-benzo[e][1,3] oxazin-4-one, 3-(6-(4-isopropyl-4H-1,2,4-triazol-3-yl) pyridin-2-yl)-7-methyl-6-(pyrimidin-5-yl)-2,3-dihydro-4H-benzo[e][1,3]oxazin-4-one, and 3-(6-(4-isopropyl-4H-1,2,4-triazol-3-yl)pyridin-2-yl)-7-methyl-6-(2-(methylthio) pyrimidin-5-yl)-2,3-dihydro-4H-benzo[e][1,3]oxazin-4-one.

10. The compound or the pharmaceutically acceptable salt thereof according to claim 1, wherein the compound is selected from the group consisting of:

3-(6-(4-isopropyl-4H-1,2,4-triazol-3-yl)pyridin-2-yl)-6-(4-(methylsulfonyl)phenyl)-2,3-dihydro-4H-benzo[e][1,3]oxazin-4-one, 3-(6-(4-isopropyl-4H-1,2,4-triazol-3-yl)pyridin-2-yl)-6-(1-(tetrahydrofuran-3-yl)-1H-pyrazol-4-yl)-2,3-dihydro-4H-benzo [e][1,3]oxazin-4-one, 6-(1-(1-ethoxyethyl)-1H-pyrazol-4-yl)-3-(6-(4-isopropyl-4H-1,2,4-triazol-3-yl)pyridin-2-yl)-2,3-dihydro-4H-benzo[e][1,3]oxazin-4-one, 1-(4-(3-(6-(4-isopropyl-4H-1,2,4-triazol-3-yl)pyridin-2-yl)-4-oxo-3,4-dihydro-2H-benzo[e][1,3]oxazin-6-yl) phenyl)cyclopropanecarbonitrile, 3-(6-(4-isopropyl-4H-1,2,4-triazol-3-yl)pyridin-2-yl)-7-methyl-6-(2-(methylthio)pyrimidin-5-yl)-2,3-dihydro-4H-benzo[e][1,3]oxazin-4-one, 3-(6-(4-isopropyl-4H-1,2,4-triazol-3-yl) pyridin-2-yl)-7-methyl-6-(1-(tetrahydrofuran-3-yl)-1H-pyrazol-4-yl)-2,3-dihydro-4H-benzo [e][1,3]oxazin-4-one, and 6-(1-(1-ethoxyethyl)-1H-pyrazol-4-yl)-3-(6-(4-isopropyl-4H-1,2,4-triazol-3-yl)pyridin-2-yl)-7-methyl-2,3-dihydro-4H-benzo[e][1,3]oxazin-4-one.

11. The compound or the pharmaceutically acceptable salt thereof according to claim 1, wherein the compound is selected from the group consisting of:

3-(6-(4-isopropyl-4H-1,2,4-triazol-3-yl)pyridin-2-yl)-6-(4-(methylsulfonyl)phenyl)-2,3-dihydro-4H-benzo[e][1,3]oxazin-4-one, 1-(4-(3-(6-(4-isopropyl-4H-1,2,4-triazol-3-yl)pyridin-2-yl)-4-oxo-3,4-dihydro-2H-benzo[e][1,3]oxazin-6-yl) phenyl)cyclopropanecarbonitrile, and 6-(4-((1H-pyrazol-1-yl)methyl)phenyl)-3-(6-(4-isopropyl-4H-1,2,4-triazol-3-yl)pyridin-2-yl)-2,3-dihydro-4H-benzo[e][1,3]oxazin-4-one.

12. The compound or the pharmaceutically acceptable salt thereof according to claim 1, wherein the compound is:

3-(6-(4-isopropyl-4H-1,2,4-triazol-3-yl)pyridin-2-yl)-6-(4-methylpyrimidin-2-ylamino)-2,3-dihydro-4H-benzo[e][1,3]oxazin-4-one.

13. The compound or the pharmaceutically acceptable salt thereof according to claim 1, wherein the compound is:

3-(6-(4-isopropyl-4H-1,2,4-triazol-3-yl)pyridin-2-yl)-6-(pyridin-4-yl)-2,3-dihydro-4H-benzo[e][1,3]oxazin-4-one.

14. The compound or the pharmaceutically acceptable salt thereof according to claim 1, wherein the compound is selected from the group consisting of:

3-(6-(4-isopropyl-4H-1,2,4-triazol-3-yl)pyridin-2-yl)-6-(1-(tetrahydrofuran-3-yl)-1H-pyrazol-4-yl)-2,3-dihydro-4H-benzo[e][1,3]oxazin-4-one, and 6-(1-(1-ethoxyethyl)-1H-pyrazol-4-yl)-3-(6-(4-isopropyl-4H-1,2,4-triazol-3-yl)pyridin-2-yl)-2,3-dihydro-4H-benzo[e][1,3]oxazin-4-one.

15. The compound or the pharmaceutically acceptable salt thereof according to claim 1, wherein the compound is selected from the group consisting of:

6-(1-isopentyl-1H-pyrazol-4-yl)-3-(6-(4-isopropyl-4H-1,2,4-triazol-3-yl)pyridin-2-yl)-2,3-dihydro-4H-benzo[e][1,3]oxazin-4-one, and 6-(1-(cyclopropylmethyl)-1H-pyrazol-4-yl)-3-(6-(4-isopropyl-4H-1,2,4-triazol-3-yl)pyridin-2-yl)-7-methyl-2,3-dihydro-4H-benzo[e][1,3]oxazin-4-one.

16. The compound or the pharmaceutically acceptable salt thereof according to claim 1, wherein the compound is selected from the group consisting of:

3-(6-(4-isopropyl-4H-1,2,4-triazol-3-yl)pyridin-2-yl)-7-methyl-6-(pyrimidin-5-yl)-2,3-dihydro-4H-benzo[e][1,3]oxazin-4-one, and 3-(6-(4-isopropyl-4H-1,2,4-triazol-3-yl)pyridin-2-yl)-7-methyl-6-(2-(methylthio)pyrimidin-5-yl)-2,3-dihydro-4H-benzo[e][1,3]oxazin-4-one.

17. The compound or the pharmaceutically acceptable salt thereof according to claim 1, wherein the compound is selected from the group consisting of:

3-(6-(4-isopropyl-4H-1,2,4-triazol-3-yl)pyridin-2-yl)-7-methyl-6-(1-(tetrahydrofuran-3-yl)-1H-pyrazol-4-yl)-2,3-dihydro-4H-benzo[e][1,3]oxazin-4-one, and 6-(1-(1-ethoxyethyl)-1H-pyrazol-4-yl)-3-(6-(4-isopropyl-4H-1,2,4-triazol-3-yl)pyridin-2-yl)-7-methyl-2,3-dihydro-4H-benzo[e][1,3]oxazin-4-one.

18. The compound or the pharmaceutically acceptable salt thereof according to claim 1, wherein the compound is:

1-(4-(3-(6-(4-isopropyl-4H-1,2,4-triazol-3-yl)pyridin-2-yl)-4-oxo-3,4-dihydro-2H- benzo[e][1,3]oxazin-6-yl) phenyl)cyclopropanecarbonitrile.

19. The compound or the pharmaceutically acceptable salt thereof according to claim 1, wherein the compound is:

6-(4-((1H-pyrazol-1-yl) methyl)phenyl)-3-(6-(4-isopropyl-4H-1,2,4-triazol-3-yl)pyridin-2-yl)-2,3-dihydro-4H-benzo[e][1,3]oxazin-4-one.

20. A compound selected from the group consisting of:

3-(6-(4-isopropyl-4H-1,2,4-triazol-3-yl)pyridin-2-yl)-6-(4-(methylsulfonyl) phenyl)-2,3-dihydro-4H-benzo[e][1,3]oxazin-4-one, 3-(6-(4-isopropyl-4H-1,2,4-triazol-3-yl)pyridin-2-yl)-6-(1-(tetrahydrofuran-3-yl)-1H-pyrazol-4-yl)-2,3-dihydro-4H-benzo[e][1,3]oxazin-4-one, 6-(1-(1-ethoxyethyl)-1H-pyrazol-4-yl)-3-(6-(4-isopropyl-4H-1,2,4-triazol-3-yl) pyridin-2-yl)-2,3-dihydro-4H-benzo [e][1,3] oxazin-4-one, 6-(1-isopentyl-1H-pyrazol-4-yl)-3-(6-(4-isopropyl-4H-1,2,4-triazol-3-yl)pyridin-2-yl)-2,3-dihydro-4H-benzo[e][1,3]oxazin-4-one, 1-(4-(3-(6-(4-isopropyl-4H-1,2,4-triazol-3-yl)pyridin-2-yl)-4-oxo-3,4-dihydro-2H-benzo[e][1,3]oxazin-6-yl) phenyl)cyclopropanecarbonitrile, 6-(4-((1H-pyrazol-1-yl)methyl)phenyl)-3-(6-(4-isopropyl-4H-1,2,4-triazol-3-yl)pyridin-2-yl)-2,3-dihydro-4H-benzo[e][1,3]oxazin-4-one, 6-(1-(cyclopropylmethyl)-1H-pyrazol-4-yl)-3-(6-(4-isopropyl-4H-1,2,4-triazol-3-yl)pyridin-2-yl)-7-methyl-2,3-dihydro-4H-benzo[e][1,3]oxazin-4-one, 3-(6-(4-isopropyl-4H-1,2,4-triazol-3-yl)pyridin-2-yl)-7-methyl-6-(pyrimidin-5-yl)-2,3-dihydro-4H-benzo[e][1,3]oxazin-4-one, 3-(6-(4-isopropyl-4H-1,2,4-triazol-3-yl)pyridin-2-yl)-7-methyl-6-(2-(methylthio) pyrimidin-5-yl)-2,3-dihydro-4H-benzo[e][1,3]oxazin-4-one, 3-(6-(4-isopropyl-4H-1,2,4-triazol-3-yl)pyridin-2-yl)-7-methyl-6-(1-(tetrahydrofuran-3-yl)-1H-pyrazol-4-yl)-2,3-dihydro-4H-benzo[e][1,3]oxazin-4-one, and 6-(1-(1-ethoxyethyl)-1H-pyrazol-4-yl)-3-(6-(4-isopropyl-4H-1,2,4-triazol-3-yl)pyridin-2-yl)-7-methyl-2,3-dihydro-4H-benzo[e][1,3]oxazin-4-one, or a pharmaceutically acceptable salt thereof.

* * * * *